United States Patent
Räisänen et al.

(10) Patent No.: US 11,908,576 B2
(45) Date of Patent: Feb. 20, 2024

(54) WEARABLE SENSOR AND HEALTHCARE MANAGEMENT SYSTEM USING A WEARABLE SENSOR

(71) Applicant: Emfit Oy, Vaajakoski (FI)

(72) Inventors: Heikki Räisänen, Oulainen (FI); Mikko Alasaukko-oja, Jyväskylä (FI); Jukka Ranta, Espoo (FI); Timo Aittokoski, Jyväskylä (FI); Jouni Mitjonen, Lehmo (FI); Tomi Virtanen, Frankfurt (DE)

(73) Assignee: EMFIT OY, Vaajakoski (FI)

( * ) Notice: Subject to any disclaimer, the term of this patent is extended or adjusted under 35 U.S.C. 154(b) by 300 days.

(21) Appl. No.: 16/836,804

(22) Filed: Mar. 31, 2020

(65) Prior Publication Data
US 2020/0312453 A1    Oct. 1, 2020

Related U.S. Application Data

(60) Provisional application No. 62/827,097, filed on Mar. 31, 2019.

(51) Int. Cl.
*G16H 40/67* (2018.01)
*G16H 10/60* (2018.01)
(Continued)

(52) U.S. Cl.
CPC .......... *G16H 40/67* (2018.01); *A61B 5/1102* (2013.01); *A61B 5/6802* (2013.01);
(Continued)

(58) Field of Classification Search
None
See application file for complete search history.

(56) References Cited

U.S. PATENT DOCUMENTS

| 4,625,733 A | 12/1986 | Saynajakangas |
| 5,486,818 A | 1/1996 | Loponen |

(Continued)

FOREIGN PATENT DOCUMENTS

| TW | 201733522 A | * 10/2017 | .......... A61B 5/0015 |
| WO | 2016110804 A1 | 7/2016 | |

(Continued)

OTHER PUBLICATIONS

Article "Accuracy of the Suunto system for heart rate variability analysis during a tilt-test" authored by Anthony Bouillod et al, published Revista Brasileira Cineantropometria e Desempenho Humanu, published 2015, edition 17(4), pp. 409-417.
(Continued)

*Primary Examiner* — Adolf Dsouza
(74) *Attorney, Agent, or Firm* — Hassan Abbas Shakir; Shakir Law PLLC

(57) ABSTRACT

A healthcare management system for a healthcare team caring for a patient to serve a healthcare need of the patient includes a wearable sensor worn by the patient for obtaining healthcare data from the patient; a healthcare clinical system having an healthcare analysis subsystem for analyzing the healthcare data; and a relay device in communication selectively with the wearable sensor and the healthcare clinical system. The healthcare analysis subsystem includes an artificial intelligence (AI) engine, the AI engine having a plurality of clinical analysis modules, each clinical analysis module is directed to a respective predetermined medical area, the respective clinical analysis module analyzing the healthcare data with a respective learned algorithm directed to the respective predetermined medical area.

20 Claims, 15 Drawing Sheets

(51) Int. Cl.
- A61B 5/11 (2006.01)
- A61B 5/00 (2006.01)
- H04W 4/80 (2018.01)
- G06F 3/01 (2006.01)
- H04W 4/14 (2009.01)

(52) U.S. Cl.
CPC ............ *A61B 5/6823* (2013.01); *A61B 5/747* (2013.01); *G06F 3/016* (2013.01); *G16H 10/60* (2018.01); *H04W 4/14* (2013.01); *H04W 4/80* (2018.02)

(56) References Cited

U.S. PATENT DOCUMENTS

| | | | |
|---|---|---|---|
| 5,611,346 | A | 3/1997 | Heikkila et al. |
| 5,628,324 | A | 5/1997 | Sarbach |
| 5,690,119 | A | 11/1997 | Rytky et al. |
| 5,719,825 | A | 2/1998 | Dotter |
| 6,104,947 | A | 8/2000 | Heikkila et al. |
| 6,277,080 | B1 | 8/2001 | Nissila et al. |
| 6,361,502 | B1 | 3/2002 | Puolakanaho et al. |
| 6,405,077 | B1 | 6/2002 | Birnbaum et al. |
| 6,418,394 | B1 | 7/2002 | Puolakanaho et al. |
| 6,477,397 | B1 | 11/2002 | Ronkainen et al. |
| 6,537,227 | B2 | 3/2003 | Kinnunen et al. |
| 6,666,562 | B2 | 12/2003 | Nissilä |
| 6,714,812 | B1 | 3/2004 | Karjalainen et al. |
| D492,784 | S | 7/2004 | Lax |
| D492,999 | S | 7/2004 | Lax |
| 6,916,979 | B2 | 7/2005 | Raisanen |
| 6,996,891 | B1 | 2/2006 | Raisänen |
| 7,216,417 | B2 | 5/2007 | Raisanen |
| 7,808,395 | B2 | 10/2010 | Raisanen |
| 7,954,385 | B2 | 6/2011 | Raisanen |
| 2011/0004072 | A1* | 1/2011 | Fletcher ............... A61B 5/6804 600/300 |
| 2012/0330109 | A1 | 12/2012 | Tran |
| 2013/0173302 | A1 | 7/2013 | Hyde et al. |
| 2015/0178629 | A1 | 6/2015 | Reifman |

FOREIGN PATENT DOCUMENTS

| | | | |
|---|---|---|---|
| WO | 2017179073 | A1 | 10/2017 |
| WO | 2019028196 | A1 | 2/2019 |

OTHER PUBLICATIONS

Article "Ballistocardiogram Signal Processing: A Literature Review" authored by Ibrahim Sadek, published Jul. 3, 2018 on arxiv.org/abs/1807.00951.

Article "Contact-Free Piezo Electric Sensor used for Real-Time Analysis of Inter Beat Interval Series" authored by Yaniv Katz et al., published 2016 in Computing in Cardiology 2016; vol. 43.

Article "Effects of sensor type and sensor location on signal quality in bed mounted ballistocardiographic heart rate and respiration monitoring", authored by Antti Vehkaoja et al., published 2015, retrieved from tutcris.tut.fi/portal/files/3924267/Effects_of_Sensor_Type_and_Sensor_Location_on_Signal_Quality_in_Bed_Mounted_Ballistocardiographic_Heart_Rate_and_Respiration_Monitoring.pdf.

Selected printout of electrodes, monitors,& sensors from sleepreviewmag.com, believed to have been published on or before Dec. 31, 2016.

Article "Firstbeat Bodyguard 2 Guide" authored by Firstbeat Technologies Oy, retrieved Dec. 9, 2019 from www.firstbeat.com/wp-content/uploads/2015/10/150811_Bodyguard2_Guide_ENG.pdf, believed to have been published on or before Dec. 31, 2015.

Article "HRV Standard" authored by Kubios Oy, retrieved Dec. 9, 2019 from www.kubios.com/downloads/Kubios-HRV-Standard.pdf, believed to have been published on or before Dec. 31, 2014.

"RS800CX User Manual", authored by Polar Electro Oy, believed to have been published on or before Aug. 31, 2013.

"Polar RS800sd A complete training system for runners and endurance athletes", authored by Polar Electro Oy, believed to have been published on or before Aug. 31, 2013.

Doctoral Thesis "Sleep Assessment Using Bed-Mounted Sensors", authored by Daniel Waltisberg, Published by ETH Zurich, Switzerland, believed to have been published on or before Dec. 31, 2017.

"Unobtrusive Online Monitoring of Sleep at Home", authored by Joonas Paalasmaa, presented 34th Annual International Conference of the IEEE EMBS San Diego, California USA, Aug. 28-Sep. 1, 2012.

"The Actiheart User Manual" Issue Version 4.0.35, Dated Jan. 7, 2010, 95 pgs.

International Search Report in patent application PCT/US2020/026037 dated Jun. 25, 2020 by the Russian Federal Institute of Industrial Property, in English.

Written Opinion of the International Search Authority patent application PCT/US2020/026037 dated Jun. 25, 2020 by the Russian Federal Institute of Industrial Property, in English.

Extended European Search Report in EPO application 20781828.7 issued by the European Patent Office dated Nov. 4, 2022.

\* cited by examiner

WEARABLE SENSOR AND HEALTHCARE MANAGEMENT SYSTEM USING A WEARABLE SENSOR

BACKGROUND OF THE INVENTION

1. Field of the Invention

The invention is directed to healthcare management system that includes a plurality of sensor and artificial intelligence to guide a healthcare team in maintaining or improving the health of a patient or prevent deterioration of the patient. More particularly, the invention is directed to a wearable sensor having a plurality of sensor integrated with a printed circuit board, a relay device, and an artificial intelligence engine.

2. Background of the Invention

In the healthcare field, patients die because signs of physical deterioration are missed, overlooked, are not detected in time, or are not detected at all. One reasons is that the intensity of patient care and frequency of vital signs monitoring is high in a professional care setting, but both markedly decrease in a non-professional care setting, such as the patient's home. Therein, it is recognized in the healthcare field that early detection of physiological instability as indicated by changes in one or more vital signs is crucial to avert disability of death of a patient.

Thus, a significant unfulfilled need exists for better monitoring of vital signs of patients in a care setting, especially in a non-professional care setting. A need also exists to obtain data from a patient that improves care of the patient in a care setting through data analysis and consistent improvement.

SUMMARY OF THE INVENTION

These and other needs are met by the present invention.

A healthcare management system for a healthcare team caring for a patient to serve a healthcare need of the patient comprises
- a wearable sensor worn by the patient for obtaining healthcare data from the patient;
- a healthcare clinical system comprising an healthcare analysis subsystem for analyzing the healthcare data; and
- a relay device in communication selectively with the wearable sensor and the healthcare clinical system;
- wherein the healthcare analysis subsystem comprises an artificial intelligence (AI) engine, the AI engine comprising a plurality of clinical analysis modules, each clinical analysis module directed to a respective predetermined medical area, the respective clinical analysis module analyzing the healthcare data with a respective learned algorithm directed to the respective predetermined medical area.

Each clinical analysis module comprises software interfaces for incoming healthcare data and outgoing processed data to integrate the respective clinical analysis module into the AI engine.

An artificial intelligence (AI) factory automatically evolves the plurality of clinical analysis modules, the AI factory replaces an existing clinical analysis module of the plurality of clinical analysis modules with a new clinical analysis module comprises a new model parameter directed to the respective predetermined medical area.

An artificial intelligence (AI) factory automatically evolves the plurality of clinical analysis modules, the AI factory replaces an existing clinical analysis module of the plurality of clinical analysis modules with a new clinical analysis module that causes fewer false alarms when serving the healthcare need of the patient.

The healthcare management system
- further comprises an artificial intelligence (AI) factory for automatic evolution of the plurality of clinical analysis modules, such that
- the relay forwards an alarm even related to the healthcare data of the patient to the healthcare clinical system; and
- the AI factory comprises an artificial intelligence learning program learning from a feedback of healthcare team relative to an accuracy of the alarm event.

An electronic medical record system comprises laboratory results related to the healthcare need of the patient.

The healthcare management system includes a clinical analysis module comprising a feature extractor submodule that selects relavant healthcare data to improve the respective learned algorithm.

The healthcare management system includes a clinical analysis module, each clinical analysis module comprises a feature extractor submodule that selects relevant healthcare data to predict an adverse medical event for the patient.

The healthcare clinical system comprises a patient database, a message queue subsystem, a notifications and messages service subsystem, SMS service subsystem, or an email service subsystem.

A patient database is a multi-node server cluster to prevent loss of a software stack or compromise patient safety.

The healthcare management system is configure so that
- the wearable sensor comprises three different patient sensors selected from the group of an electrocardiogram (ECG) sensor, a ballistocardiogram (BCG) sensor, a photoplethysmography (PPG) sensor, a skin temperature (TEMP) sensor, a motion and position sensor, and electrodermal (EDA) sensor;
- the motion and position sensor comprises an accelerometer and a gyroscope;
- the three different sensors are operatively integrated on a printed circuit board.

The healthcare management system includes
- a chest band for securing the wearable sensor to a chest of the patient,
- a charging pad for wirelessly charging the wearable sensor; and
- a haptic feedback device to alert the patient.

A haptic feedback device alerts the patient to the relay to attend to an information request from the healthcare team.

The healthcare management system is configured such that
- the wearable sensor comprises a patient sensor selected from the group of an electrocardiogram (ECG) sensor, a ballistocardiogram (BCG) sensor, a photoplethysmography (PPG) sensor, a skin temperature (TEMP) sensor, a motion and position sensor, and electrodermal (EDA) sensor;
- the patient sensor determines measurement data from a signal obtained by the sensor and calculates extracted quantitative data, the extracted quantitative data being transmitted as healthcare data to the healthcare clinical system.

The wearable sensor comprises a ballistocardiogram (BCG) sensor, the BCG sensor being used to calculate a respiration rate, a respiration volume, a heart rate, and a heart stroke volume, and providing data for blood pressure calculations.

The relay and the wearable sensor are in communication via Bluetooth.

The relay and the healthcare clinical system are in communication via a cellular data network.

The wearable sensor and the healthcare clinical system are in communication via a cellular data network.

DETAILED DESCRIPTION OF THE INVENTION

General Conditions

Figure 1:
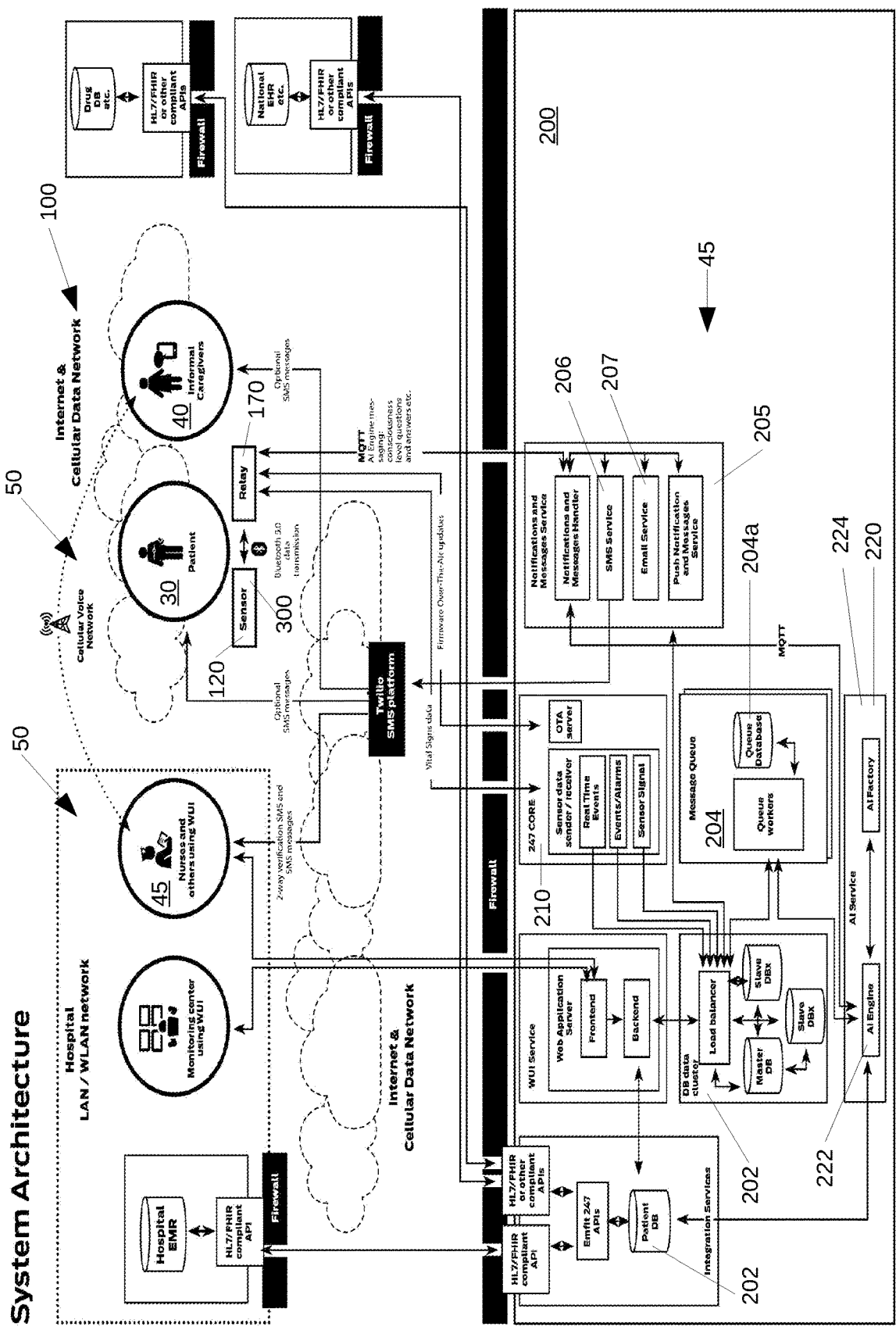
FIG. 1 is a schematic view of the healthcare management system in accordance with one or more embodiments of the present invention.

This disclosure and the description of the invention is provided to assist in an understanding of various embodiments of as defined by the claims and their equivalents. The embodiments are merely exemplary and various changes and modifications of the various embodiments may be made without departing from the scope and spirit of the invention.

Measurements may be given using a comma format and, thus, its equivalent in period format is readily apparent. Therein, for example, a dimension of 0.1 mm (comma format) means 0.1 mm (period format).

One or more embodiments may be combined with one or more other embodiments. Where one unit of an item is disclosed, more than one unit of that item may be used for at least the reason of economic efficiency. Conversely, where more than one unit of an item is disclosed, only one unit of that item may be used for at least the reason of economy, space-saving, manufacturing efficiency, and/or power consumption.

Definitions

All technical and scientific terms shall have the same meaning as commonly understood by one of ordinary skill in the art. Nonetheless, the following terms are defined below to aid in the understanding of the disclosure and the definitions apply to all parts of speech of the term regardless whether the term is defined explicitly as such. The terms defined herein should be construed in a non-limiting way.

The terms "about," "approximately," or "substantially similar" refer to a 10% variation from the nominal value. The requisite term is to be understood to include a variation in a given value, whether or not the variation is specifically referenced.

"2D" means two dimensions and/or two-dimensional while"3D" means three dimensions and/or three-dimensional.

"Biocompatible" or "biocompatibility" is a property of a material that defines the material as being compatible with living tissue. Biocompatible materials do not produce a toxic or immunological response when exposed to the body or bodily fluids.

Forms of the verb "to capture" mean to (a) acquire signal of an object through one or more sensors or portions of sensors, and (b) save that signal as data to a file having any suitable format to any suitable memory storage.

"Computing device," or interchangeably "hardware," is intended in this disclosure for all purposes to be interpreted broadly and is defined for all uses, all devices, and/or all systems and/or systems in this disclosure as a device comprising at least a central processing unit, a communications device for interfacing with a data network, transitory computer-readable memory, and/or a non-transitory computer-readable memory and/or media. The central processing unit carries out the instructions of one or more computer programs stored in the non-transitory computer-readable memory and/or media by performing arithmetical, logical, and input/output operations to accomplish in whole or in part one or more steps of any method described herein.

A computing device is usable by one or more users, other computing devices directly and/or indirectly, actively and/or passively for one or more suitable functions herein. The computing device may be embodied as computer, a laptop, a tablet computer, a smartphone, and/or any other suitable device and may also be a networked computing device, a server, or the like. Where beneficial, a computing device preferably includes one or more human input devices such as a computer mouse and/or keyboard and one or more human interaction device such as one or more monitors. A computing device may refer to any input, output, and/or calculating device associated with providing a virtual reality experience to one or more users.

Although one computing device may be shown and/or described, multiple computing devices may be used. Conversely, where multiple computing devices are shown and/or described, a single computing device may be used.

"Computer program," or interchangeably "software" or "firmware," means any set of instructions stored in a non-transitory computer-readable memory or non-transitory computer-readable media for executing one or more suitable functions and/or for executing one or more methods in this disclosure. Even if not explicitly mentioned, in this disclosure, a computing device includes software having any set of instructions stored in non-transitory computer-readable memory or non-transitory computer-readable media for executing one or more suitable functions and/or for executing one or more methods in this disclosure.

"Computer system," or interchangeably "system" means a plurality of interoperable computing device linked by one or more "communications devices," which may be arranged in a "communications network." The communications devices and/or the communications network may use any communications form now known or yet to be devised or invented; for example, electronic or optical, wired or wireless, cellular data or voice, local area network, wide-area network, metropolitan area network, near-field, internet, cloud, bluetooth, or infrared. Where necessary or advantageous, one or more software or hardware firewalls are installed, provided, or in some other way made accessible to or to work with one or more computer systems and/or communications devices to isolate each from another from one or more other computer systems and/or communications devices to prevent intrusion of any kind, malice of any kind, and/or theft or unauthorized access of data.

"Healthcare" means care undertaken of a "patient" by one or more "caregivers," who may be trained or untrained persons, i.e. an informal caregiver, to restore the physical and/or mental health of the patient in a "care setting," which may be a professional setting of a hospital, hospital ward, private clinic, nursing home, sanitorium, psychiatric care facility, or a non-professional setting such as a home. "Healthcare" and "patient care" may be used interchangeably as required for understanding of this invention.

"Non-transitory computer-readable memory," or interchangeably "non-transitory computer-readable media," may be a hard drive, solid state drive, compact disk drive, DVD drive, and/or the like for storing the one or more computer programs.

"Participant" or interchangeably "participants" means one more users of the present invention who have been given one or more privilege to use the one or more systems of the present invention after being authorized, authenticated, credentialed, verified, and/or permitted using any suitable means now known or to be devised. The privilege may be conditional, permanent, temporary, or single-use and/or may be subject review and/or revocation as may be determined by one or more other participants.

"Patient" and "wearer" may be used interchangeably as required for understanding of this invention.

"Subsystem" means a computer system, as defined elsewhere herein, that is subservient and/or integrated in a larger computer system, but may act independent of the computer system when so instructed by a user or another computer system.

"Wearable" means that the item that is being worn has physical dimensions, properties of heat, coldness, texture, and weight that are suitable for the anatomy of the wearer and/or strength of the wearer as commonly understood by one skilled in the art.

Healthcare Management System

FIG. 1 is a schematic view of the healthcare management system in accordance with one or more embodiments of the present invention.

The invention is directed to healthcare management system that includes a plurality of sensor and artificial intelligence to guide a healthcare team in maintaining or improving the health of a patient or prevent deterioration of the patient, i.e. serve the healtcare needs of the patient. More particularly, the invention is directed to a wearable sensor having a plurality of sensor integrated with a printed circuit board, a relay device, and an artificial intelligence engine.

A healthcare management system 100 includes a wearable sensor 120 having one or more sensors 140, a chest band 150, a charge pad, a relay 170, and a healthcare clinical system 200.

Healthcare monitoring system 100 includes a patient 30, who in this description is a human patient suffering from one or more physical ailments, i.e. physiological and/or medical conditions. However, patient 30 may also or instead, suffer from one or more age related frailties or diseases, psychological ailments, and/or psychiatric ailments as may be used interchangeably in this description as required for understanding of this invention. Patient 30 may also be an animal patient, such as a dog, race horse, or other suitable animal and in such cases where in this description terms such as physician or nurse are used, veterinarian or veterinarian technician or assistant may be readily substituted.

Healthcare monitoring system 100 includes a caregiver 40 operating in care setting 50. Caregiver 40 may be one or more trained or untrained persons who restore the physical and/or mental health of the patient in a care setting 50, which may be a professional setting of a hospital, hospital ward, private clinic, nursing home, sanatorium, rehabilitation clinic, psychiatric care facility, or a non-professional setting such as a home.

Healthcare team 45 may also be part of healthcare management system 100 and is preferably the most responsible healthcare authority for patient 30, i.e. final professional medical decision of the healthcare of patient 30 are taken by healthcare team 45. Healthcare team 45 may be comprised of one or more professional nurses, physician, pharmacist, rehabilitation specialists, occupational specialists, and/or other qualified medical professionals who interact with patient 30 and/or an informal caregiver 40 or a professional caregiver 40 at one or more other care setting 50. Therein, an informal caregiver 40 may be a spouse, visiting nurse, responsible child, relative, and/or parent.

Care setting 50 may also be an animal hospital or veterinary clinic or even the home of patient 30. Moreover, care setting 50 may also be a call center where one or more professional caregivers 40 or a healthcare team 45 are located to reactively or pro-actively address health related issues of patient 30. Using communications technology known in the art, healthcare team 45 and/or caregiver 40 may also whole or in part be located distal from care setting 50.

Collectively and/or individually, patient 30, caregiver 40, healthcare team 45, and care setting 50 are participants of healthcare management system 100.

Healthcare monitoring system 100 provides an intelligent detection of the deterioration of patient 30 with extremely low false-alarm using known and yet to be developed self-learning (machine learning) algorithms and artificial intelligence using comprehensive data parameter sets.

Healthcare monitoring system 100 provides the highest possible patient adherence for wearable sensor 120 which may be worn on the body of patient 30 for any time suitable and/or medically necessary, because, advantageously, wearable sensor 120 is both very comfortable and easy to use during daily activities when patient 30 is at home or other non-professional care facility rather than a professional care facility.

Wearable sensor 120 has IP67 protection against water and dust, and preferably incorporates wireless battery charging using a charge pad. Therein, wearable sensor 120 and relay 170 are safe reusable medical devices that withstand at least 2 years of normal use and remain electrically safe and biocompatible for at least that duration.

Healthcare monitoring system 100 meets European Medical Device Regulation (MDR) and meet other important regulations such as the U.S. Food and Drug Administration regulations. Therein, one or more components of healthcare management system 100 are marked with the CE compliance marking as medical devices in class 2a and/or class 2b and comply with the following standards and regulations:
1. Wearable sensor 120, a charge pad, and relay 170 comply with the Radio Equipment Directive 2014/53/EU (RED);
2. Wearable sensor 120 and relay 170, comply with Medical Device Directive 93/42/EEC (MDD) and coming Medical Device Regulation (MDR) including:
   a. EN60601-1 ed. 4 Medical Electrical equipment—Part 1: general requirements for basic safety and essential performance,
   b. EN60601-1-2 ed. 4, Medical Electrical equipment—Part 1-2: EMC,
   c. IEC62304:2015 Medical device software-software lifecycle process,
   d. IEC 62366:2007 and 1:2014 Medical devices Part 1: Application of usability engineering to medical devices,
   e. EN ISO 15223-1:2016 Symbols for use in the labelling of Medical Devices, f EN1041:2008 A1:2013 Information Supplied by the manufacturer of Medical Device, and
   g. ISO 10993-1 (ISO 10993-5, ISO 10993-10) Biocompatibility reports (cytotoxicity, skin sensitization/irritation);
3. Power source 125 preferably complies with IEC 62133-2:2012 or UL642, (safe for use), and UN 38.3 (safe for transport).

All components and materials in healthcare management system 100 are compliant with RoHS 3 Directive 2015/863/EU) and with privacy regulations, such as the GDPR in EU.

Wearable Sensor

Figure 2:
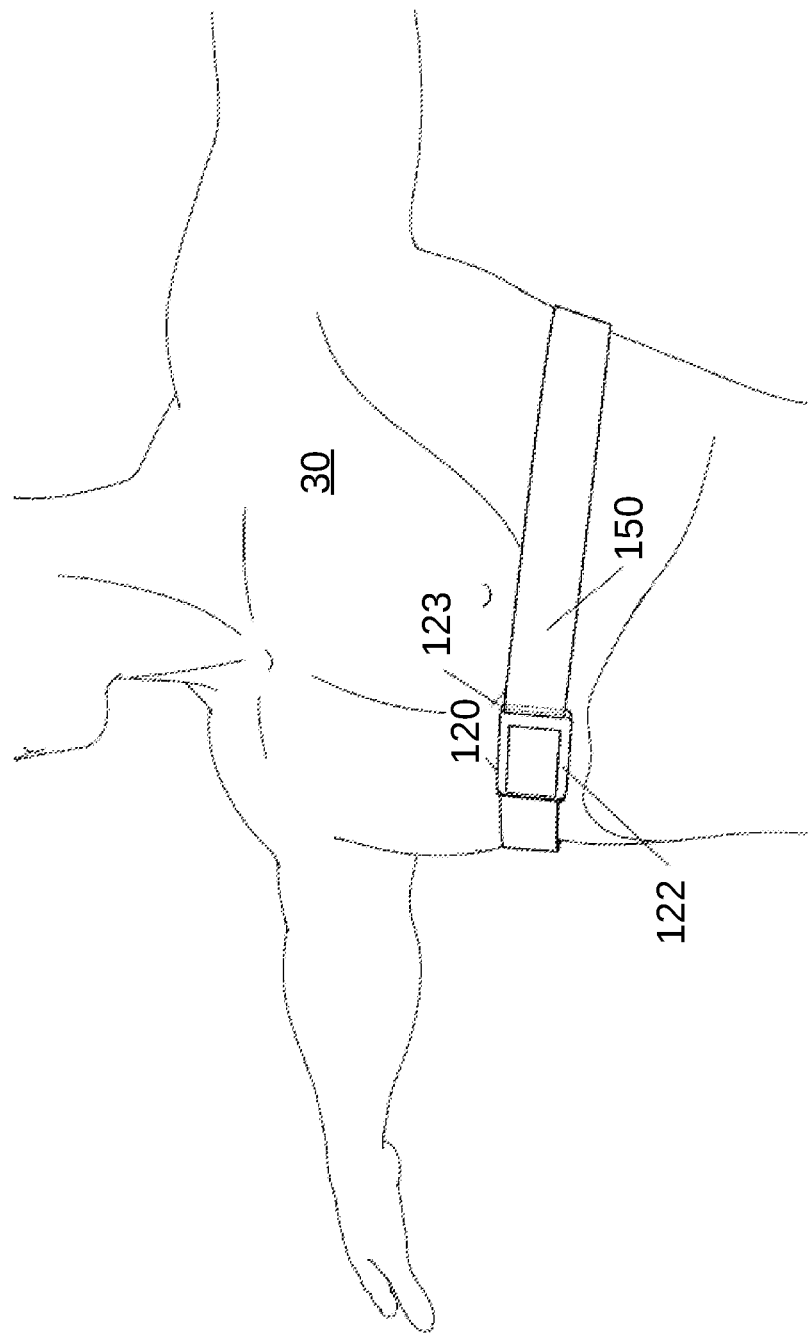
FIG. 2 is a front isometric view of a wearable sensor and a chest band as worn by a patient using the healthcare management system in accordance with one or more embodiments of the present invention.

FIG. 2 is a front isometric view of a wearable sensor and a chest band as worn by a patient using the healthcare management system in accordance with one or more embodiments of the present invention.

Figure 3A:
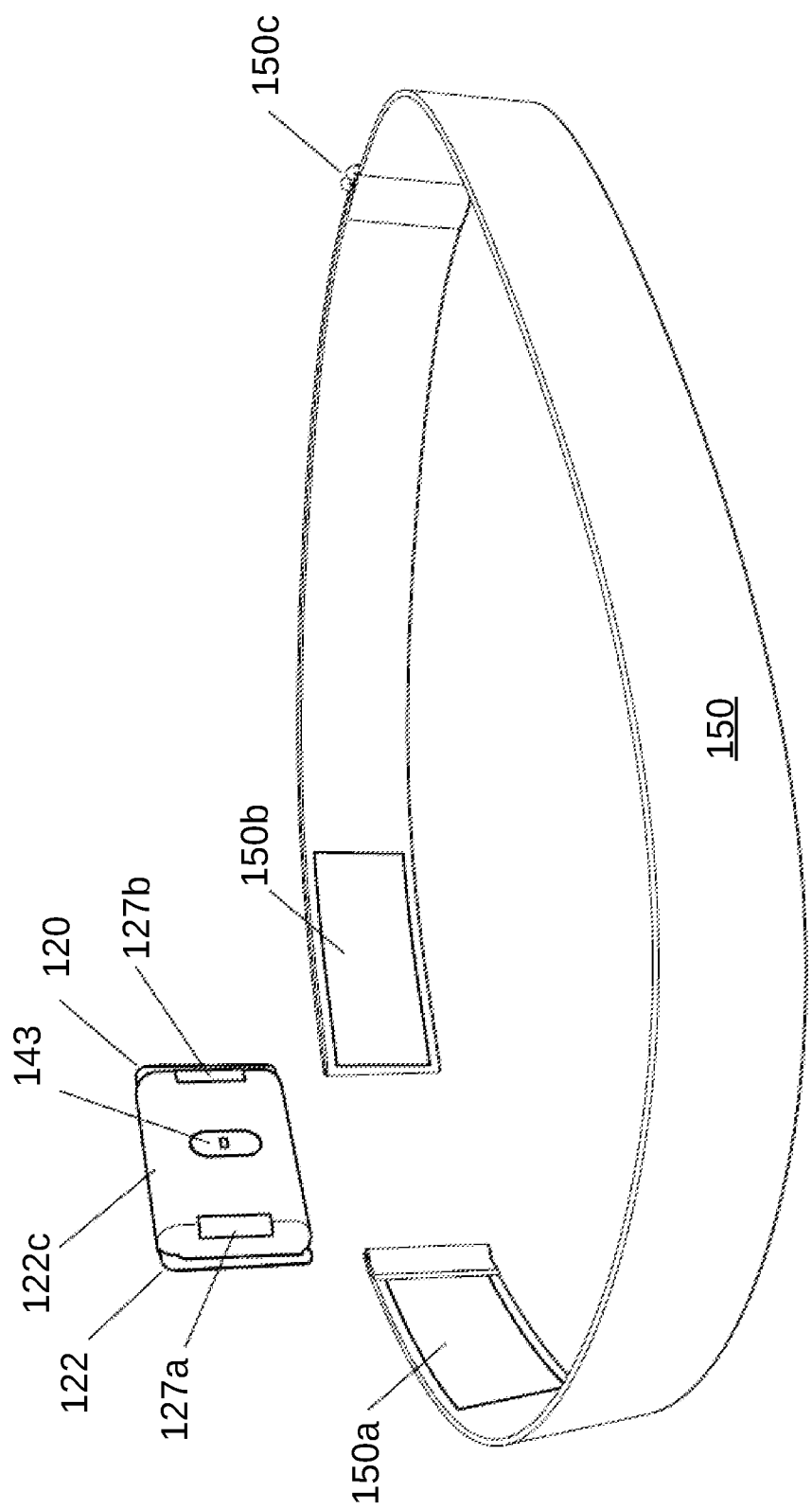
FIG. 3a is a rear isometric view of a wearable sensor and a chest band in a partially exploded illustration in accordance with one or more embodiments of the present invention.

FIG. 3a is a rear isometric view of a wearable sensor and a chest band in a partially exploded illustration in accordance with one or more embodiments of the present invention.

Figure 3B:
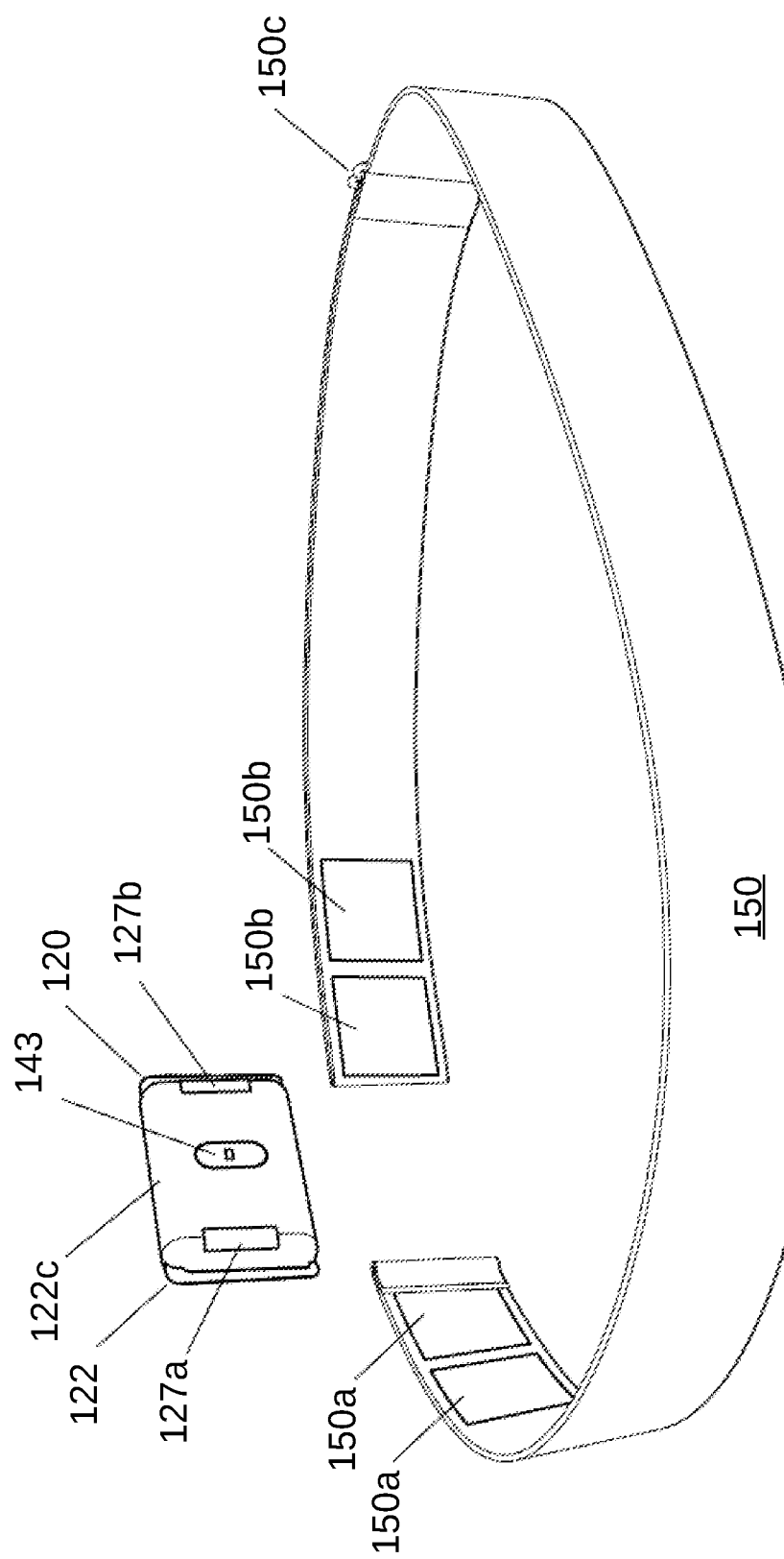
FIG. 3b is a rear isometric view of a wearable sensor and a chest band in a partially exploded illustration in accordance with another embodiment of the present invention.

FIG. 3b is a rear isometric view of a wearable sensor and a chest band in a partially exploded illustration in accordance with another embodiment of the present invention.

Figure 4A:
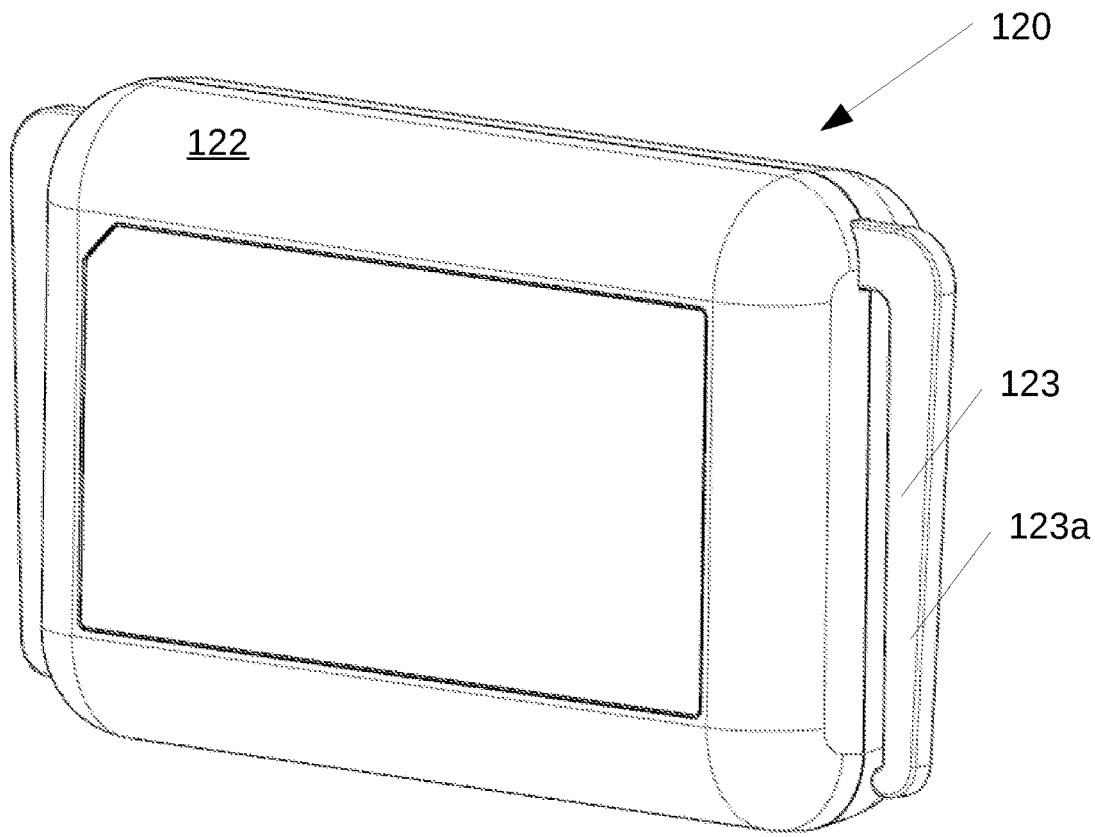
FIG. 4a is a front isometric view of a wearable sensor in accordance with one or more embodiments of the present invention.

FIG. 4a is a front isometric view of a wearable in accordance with one or more embodiments of the present invention.

Figure 4B:
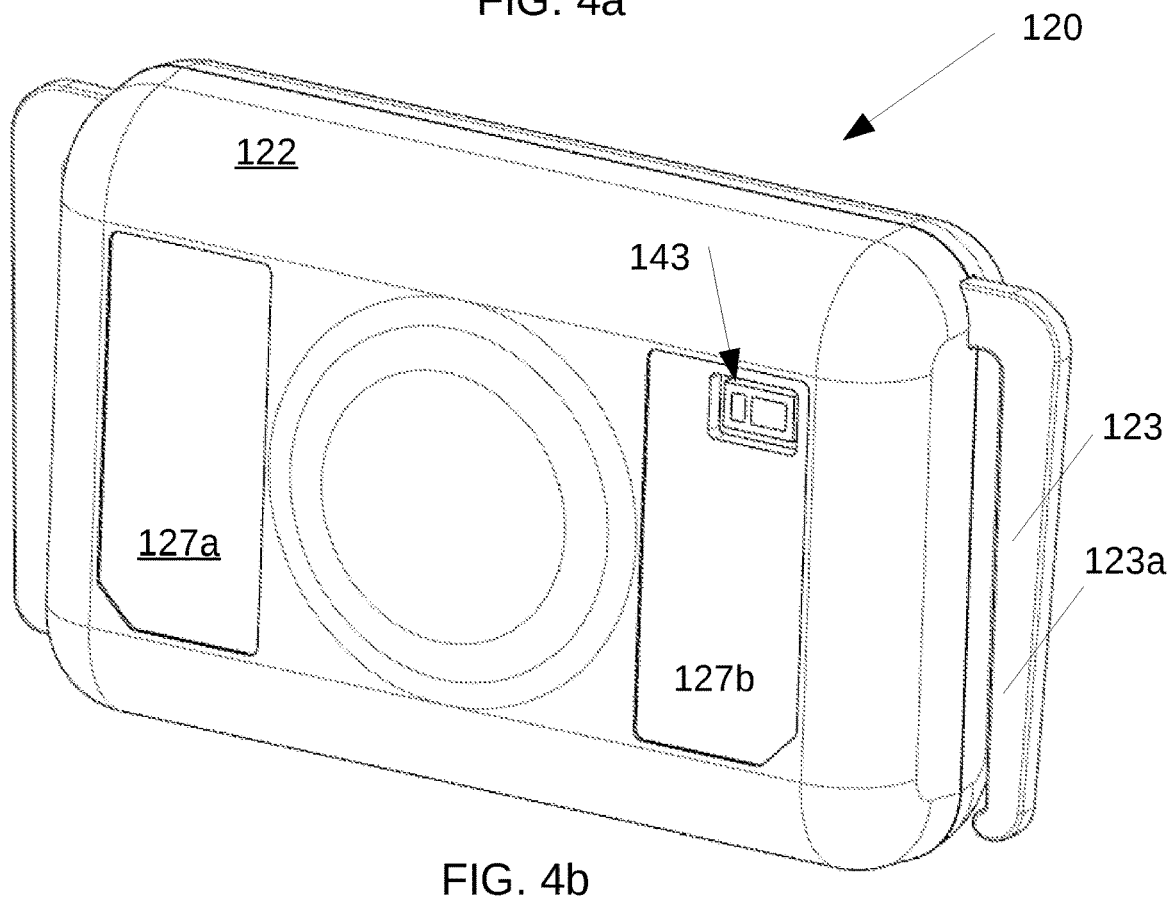
FIG. 4b is a rear isometric view of a wearable in accordance with one or more embodiments of the present invention.

FIG. 4b is an isometric view of a wearable in accordance with one or more embodiments of the present invention.

Figure 4C:
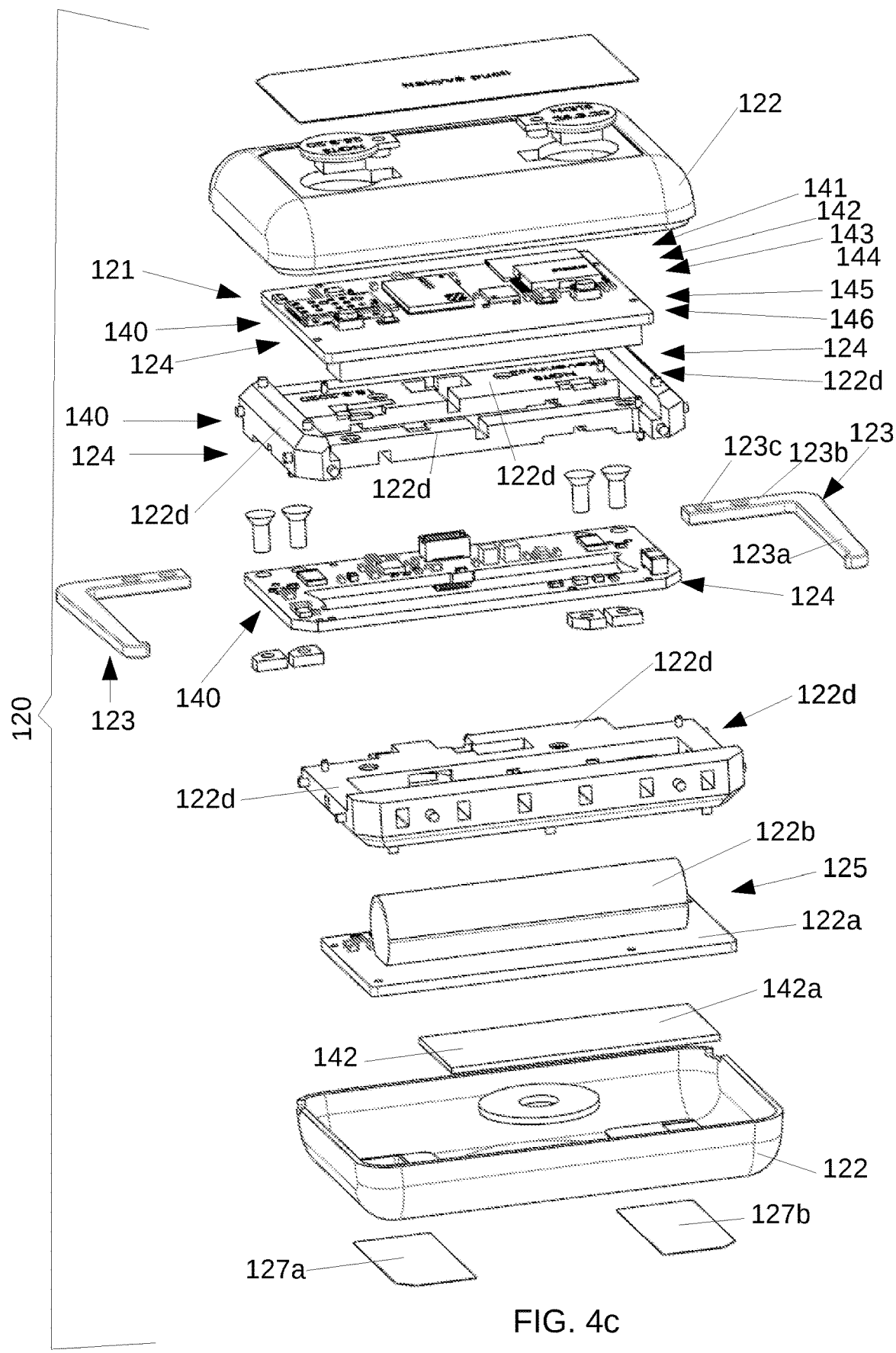
FIG. 4c is an exploded view of a wearable sensor in accordance with one or more embodiments of the present invention.

FIG. 4c is an exploded view of a wearable sensor in accordance with one or more embodiments of the present invention.

Wearable sensor 120, although described as a sensor is a sensing and/or monitoring device, or simply wearable monitor 120. It comprises one or more sensors 140 that each obtain respective measurement data from patient 30, analyze in one or more computing devices 124 the respective measurement data to obtain extracted quantitative data. Wearable sensor 120 transmits extracted quantitative data to relay 170 which in turn passes extracted quantitative data for further analysis to an intelligent data analysis system with a very low false alarm rate.

In general, wearable sensor 120 is an unobtrusive wireless sensing and/or monitoring device, i.e. monitor, that does not interfere with the daily activities and/or rehabilitation of patient 30. The shape of wearable sensor 120 may be any suitable shape, for example, box shaped, oblong, or flattened; but the shape is defined by an enclosure 122.

Wearable sensor 120 preferably lasts for over 2 years, is an IP67 classified sensor, and comprises an enclosure that encapsulates the components of wearable sensor 120 in elastic polyurethane with UL 94-v0 fire safety classification. USP Class VI Biocompatibility is achieved using biocompatible overlay, such as radiation-curing acrylate, silicone, or epoxy. Overlay is compatible at least with common disinfection and cleaning methods, and can be compatible even with sterilization methods including gamma irradiation, EtOand limited autoclaving.

Wearable sensor 120 integrates one or more sensors 140, for example, a single-lead or double-lead electrocardiogram (ECG) sensor 141, a ballistocardiogram (BCG) sensor 142, a photoplethysmography (PPG) sensor 143, a skin temperature (TEMP) sensor 144, an accelerometer (ACC) and gyroscope (GYRO), i.e. a motion and position sensor 145, and an electrodermal EDA sensor 146; and power source having large capacity 345 mAH rechargeable battery, which is rechargeable wireless Qi-standard charging pad. Wearable sensor 120 is an innovative "all-in-one", durable but light, encapsulated reusable sensor that lasts with one charge over 5 days. There is small vibration component to vibrate and notify user if provided. It is comfortable and easy to use for high level patient adherence.

In accordance with one or more embodiments of the present invention, wearable sensor 120 may be worn by patient 30 over a T-shirt, underwear, or other clothes, i.e. a thickness of 3-5 mm, if patient 30 prefers but prevents capture of oxygen saturation, and an electrocardiogram. Therein, capture of heart rate and breathing (respiratory) rate of patient 30 by as well as capture of motion and position of patient 30 by one or more sensors 140 are not affected. Capture of skin temperature by skin temperature sensor 144 is not effected, but the temperature would be slightly less. However, trend changes in skin temperature would be noticeable. Moreover, placement of wearable sensor 120 over a T-shirt or the like prevents wearable sensor 120 to damage or pull the skin of patient 30.

Moreover, the location that wearable sensor 120 is disposed on the chest of patient 30 can be adjusted to let skin directly underneath breath.

Feedback Vibrator

In accordance with one or more embodiments of the present invention, wearable sensor 120 may comprises a feedback vibrator 121, which may be any suitable feedback device whether auditory, visual, or haptic. However, preferably feedback vibrator 121 is a haptic feedback device operatively mounted on or integrated with printed circuit board 124 to provide a vibration in one or more predetermined situations to patient 30 to alert the patient including to attend to relay 170. These situations are preferably (1) when wearable sensor 120 and chest band 150 are correctly fitted at start of measuring, (2) when wearable sensor 120 and relay 170 are operatively engaged to transmit data from one to the other, (3) when a notification is sent to patient 30 and/or caregiver 40 via relay 170, and/or (4) when an information request is made or a confirmatory answer is requested, for example when healthcare team 45 notices via other means or via data in healthcare management system 100 that patient 30 is in distress.

In accordance with one or more embodiments of the present invention, feedback vibrator 121 or another communication device, such as a switch operable with printed circuit board 124, of wearable sensor 120 can make a request for assistance, such as when patient 30 is in distress.

Enclosure and Hooks

Enclosure 122 retains a computing device 124 for data processing and communications, which is preferably in the form of one or more printed circuit boards 124, hooks 123, and requisite sensors 140 as described below. While enclosure 122 may be any type of physical enclosure, such as a box of any shape and any material, it is preferable that enclosure 122 is an overmolding with a suitable material so that the wearable sensor 120—and specifically the components of wearable sensor 120, including for example printed circuit board 124 and or sensors 140—are encapsulated in a tight, water resistant manner without interference with their inherent functionality.

In accordance with one or more embodiments of the present invention, enclosure 122 is made in a single overmolding step. However, in accordance with one or more embodiments of the present invention, enclosure 122 has a first portion that results from a first overmolding step and a second portion that is slightly larger than the first portion by 0.5 to 1.0 mm that results from a second overmolding step. The two portions are joined have a tight, water resistant fit by virtue of the overmolding process.

Therein, enclosure 122 is preferably sufficiently sized to house a power source 125.

A pair of hooks 123 are preferably made of an electrically conductive material. Each has a hook portion 123a that is exterior of enclosure 122 and is not overmolded. Each hook of the pair of hooks 123 comprises a retention portion 123b that comprises one or more holes 123c through which an overmolding material flows to form enclosure 122.

Hooks 123 may also be directly connected to printed circuit board 124 via riveting of holes 123c. Instead of rivets, also small bolts and nuts can be used. Therein, advantageously, the electrical signal picked from the skin of patient 30 has a direct path to ECG sensor 141. Alternatively, silver plate or biocompatible metal electrodes may be placed in wearable sensor 120 such that the one or more biocompatible metal electrodes have respective contact surfaces flush with a rear outer surface 122c of enclosure 122. However, it is preferred to use ECG electrodes 150a, 150b disposed in the conductive fabric of chest band 150. Especially when several electrically separated electrodes (FIG. 3b) are provided, such as in a 2-lead ECG is preferred, or if both ECG and EDA measuring are provided, it may be beneficial to use both electrodes 150a, 150b at chest band 150 and electrodes 127a, 127b on the enclosure 122.

Hook portion 123a serves as an anchorage for a chest band 150 that is disposed around the torso of patient 30 and keeps wearable sensor 120 in place around the torso, i.e. chest, proximal in a line with the heart of patient 30 by frictional force and/or being suitably tightened. Where necessary, wearable sensor 120 may also be held in place line with the heart of patient 30 using suspenders reaching to chest level and/or a suitably sized harness.

In accordance with one or more embodiments of the present invention, a segment of each hook portion 123a may or may not make contact with the skin of patient 30 and may be used an electrode by itself or in combination with chest band 150 as described herein.

In accordance with one or more embodiments of the present invention, enclosure 122 of wearable sensor 120 is made by molding and, therein, may be molded from biocompatible epoxy or silicone over the entirety of enclosure 122 but not respective hook portion 123a to maintain an electrical contact surface for fabric electrodes arranged into the chest band 150.

To permit molding of enclosure 122 while permitting electrodes on the chest band 150 and PPG sensor 143 to protrude from enclosure 122, certain materials were found disadvantageous. Silicone materials are too soft for housing safely the entire electronics circuitry, and would not last long enough in use by patient 30. Similarly, epoxies alone used for encapsulation would be disadvantageous as they are too rigid and prevent ferroelectret sensor from operating. The need to provide both fire-safety and biocompatibility requires the use of two or more layers in the encapsulation. One in the core for housing electronics circuitry and other on the outer side to provide surface for skin contact.

In accordance with one or more embodiments of the present invention, enclosure 122 of wearable sensor 120 is made by a first step of overmolding computing device 124 using polyurethanes (PU) class materials to achieve structural formation of enclosure 122 and in a subsequent step applying an overlay of adhesive or silicone to achieve biocompatibility. Therein, enclosure 122 preferably has structural integrity and substantially maintains its shape yet is pliable to slightly bend to allow mechanical forces by breathing and heart beating of the patient 30 be sensed by the ferroelectret film BCG sensor 142 arranged inside the enclosure 122. Somewhat soft form factor also enables comfortable fit on the chest. Herein, the overmolding may be performed in two steps. First overmolding computing device 124 with hooks 123 attached, but sections 123a remaining outside of molding. Then secondly adding a new outer layer in a second overmolding, now using biocompatible material such as silicone from manufacturer Masterbond, type Mastersil 151.

In one or more embodiments of the invention the outer layers (shells) 122 are first separately manufactured in compression molding from biocompatible material, such as Makroblend 525 from Covestro. Shells 122 are then assembled with computing device 124 with hooks 123 attached. Then the assembly's inner remaining cavity is encapsulated by filling it with very low or no pressure, in room temperature curing poluyurethane such as Arathene.

It is important that all electronics due to the ferroelectret sensor 142 is like one solid pack because the ferroelectret sensor need to have opposite force to be able to measure ballistocardiogram (respiration and heart beat). When electronics are directly housed inside biocompatible shells, the PU encapsulation material can be poured through a hole into the inner cavity and there is no need for molds to do the PU molding (encapsulation). This will save manufacturing time significantly as the PU inside can cure itself without mold. Also as shells are directly biocompatible, there is no need to add biocompatible silicone as outermost layer. The labels can be made from biocompatible material such as Lexan® type 8040, and attached with adhesive. To reduce weight, the inner cavity preferably has one or more carefully designed, 3D printed airtight air-cavities s. These reduce PU volume to reduce overall weight for patient conformity.

Preferably, the polyurethane (PU) class material is Arathane™ from Huntsman Advanced Materials GmbH from Germany and in particular CW5620+HY561. Advantageously, CW5620+HY561 has UL 94-v0 fire safety classification, is highly elastic (65% elongation at break), cures under 80° C. and has a pot life of sufficient length. Curing under 80° C. is important to retain a ferroelectret material charge. Polyurethane (PU) class material Arathane™ provides an enough softness for ferroelectret sensor 142 operation, but is enough rigid to provide mechanical strength in long term use.

To meet biocompatibility, instead of adding silicone in a new overmolding, in a step subsequent to molding, an overlay of an acrylate can be applied to the structure formed in the first molding step. Therein, the acrylate is preferably made Panacol-Elosol GmbH and is Vitralit® 7041 acrylate. Panacol Vitralit® adhesives are one-component, solvent-free radiation-curing adhesives. Advantageously, Panacol Vitralit® adhesives have very short curing times, good adhesion to many substrates, and easy handling.

In accordance with one or more embodiments of the present invention, Vitralit® 7041 is used as the overlay because it has a low viscosity, is solvent-free, is LED light curable, highly resistant to moisture, and forms a resilient, high strength bonds between many plastics and dissimilar materials. Vitralit® 7041 has passed the testing required for USP Class VI biocompatibility approval and is compatible with common sterilization methods including gamma irradiation, EtO, and limited autoclaving.

Printed Circuit Board

Printed circuit board 124 or another computing device 124 includes a system-on-chip (SOC) for space savings and may be an SOC model nRF52840 from Nordic Semiconductors using 32-bit ARM® Cortex™-M4 CPU architecture to execute a patient monitoring software 300. In accordance with one or more embodiments of the present invention, each sensor 140 described herein associated with wearable sensor 120 is functionally connected to, connected with, or disposed on printed circuit board 124 and controlled via instructions from patient monitoring software 300.

In accordance with one or more embodiments of the present invention, measurement data is one or more data obtained from one or more objective measurements of the body of patient 30 that are analyzed by patient monitoring software 300 to obtain extracted quantitative data of patient 30.

Vital signs include heart rate, electrocardiogram (ECG) measurements, respiratory rate, pulse, skin temperature, electrodermal activities, and/or blood pressure. Vital signs along with qualitative data as embodied as a level of consciousness are key predictors of status and/or the deterioration of patient 30. That prediction is enhanced with analysis of various data from the medical record, i.e. medical record data as further described herein. Medical record data as further defined herein includes demographic data such as patient age and also biochemistry and hematology data, e.g., serum creatine (as an indicator of acute kidney injury); urea; white blood cell count, and other data obtained now While extracted quantitative data is described herein with regard to vital signs, extracted quantitative data is not limited to vital signs. Thus, measurement data that may be gleaned from an objective data via wearable sensor 120 may be extracted quantitative data. For example, extracted quantitative data may include an objective measurement of a viral load in a patient using means now known or yet to be developed.

Power Source Power source 125 may be any suitable power source that is permanent or temporary and provides sufficient power for wearable sensor 120 to be functional. Thus, power source 125 may be battery housed in a power source enclosure portion 122a and closed by a support segment 122b. Therein, power source 125 may be replaceable, but power source 125 may be a non-replaceable be chargeable using wireless charging.

In accordance with one or more embodiments of the present invention, power source 125 is a Li-ion metal cylindrical cell having AAA size, 345 mAh capacity Li-ion battery.

Electrocardiogram (ECG) Sensor

In accordance with one or more embodiments of the present invention, wearable sensor 120 may comprise a sensor 140 in the form of an electrocardiogram (ECG) sensor 141 for detecting as measurement data the electrical activity of the heart of patient 30 to produce results of voltage versus time as extracted quantitative data. ECG sensor can be arranged to the chest band, using electrically conductive fabric. If a 2-lead ECG is provided, or single-lead ECG and EDA measuring are provided, it is advantageous that some electrodes are arranged on the enclosure 122. On it the electrode 141 is in contact with the skin of patient 30 when wearable sensor 120 is worn by patient 30, and, thus, preferably comprises high quality nickel-free sterling silver at 92.5% by weight and copper at 7.5% by weight to reduce potential skin irritation.

In accordance with one or more embodiments of the present invention, ECG sensor 141 preferably is configured as a single-lead electrocardiogram sensor and does not use wired electrodes for added patient comfort and easy fit on the patient's torso, i,e, chest. As is known in the art, ECG sensors typically use wired (wet) electrodes having conductive gel pads to improve electrical contact between electrode and a patient and are excellent for diagnosing patients electrical signals for patients.

Herein, wearable sensor 120 for healthcare management system 100 is used in accordance with one or more embodiments of the present invention, for diagnosis purposes, to find R-R intervals based on extracted quantitative data from ECG sensor 141 and/or detecting atrial fibrillation (AFIB) by detecting missing p-waves. By managing the use of extracted quantitative data from ECG sensor 141, rather than using wires and gel pads, patient 30 is provided with added patient comfort and easy fit on the patient's torso, i,e, chest, by not having wires.

The ECG signal determined from ECG sensor 141 is preferably ultra-clean for a common peak detection algorithm that can be used for heart rate (HR) and heart-rate-variability (HRV) computation. One of three different HR calculation algorithms use the ECG signal. To achieve an ultra-clean ECG signal with least possible 50/60 Hz noise, signal electrodes are located the ends of ECG sensor 141 and a ground electrode is located to the middle of the sensor.

In accordance with one or more embodiments of the present invention, instead of disposing ECG electrodes on the fabric chest band, the electrodes of ECG sensor 141 may be arranged on an enclosure 122 being long and flexible and bend lengthwise to accommodate chest sizes of patient 30 while ensuring electrode contact with the skin of patient 30. Therein, ECG sensor 141 comprises electrodes that are horizontally at about heart height (from toe to head). This position is advantageous for single lead applications.

Ballistocardiography Sensor

Figure 5:
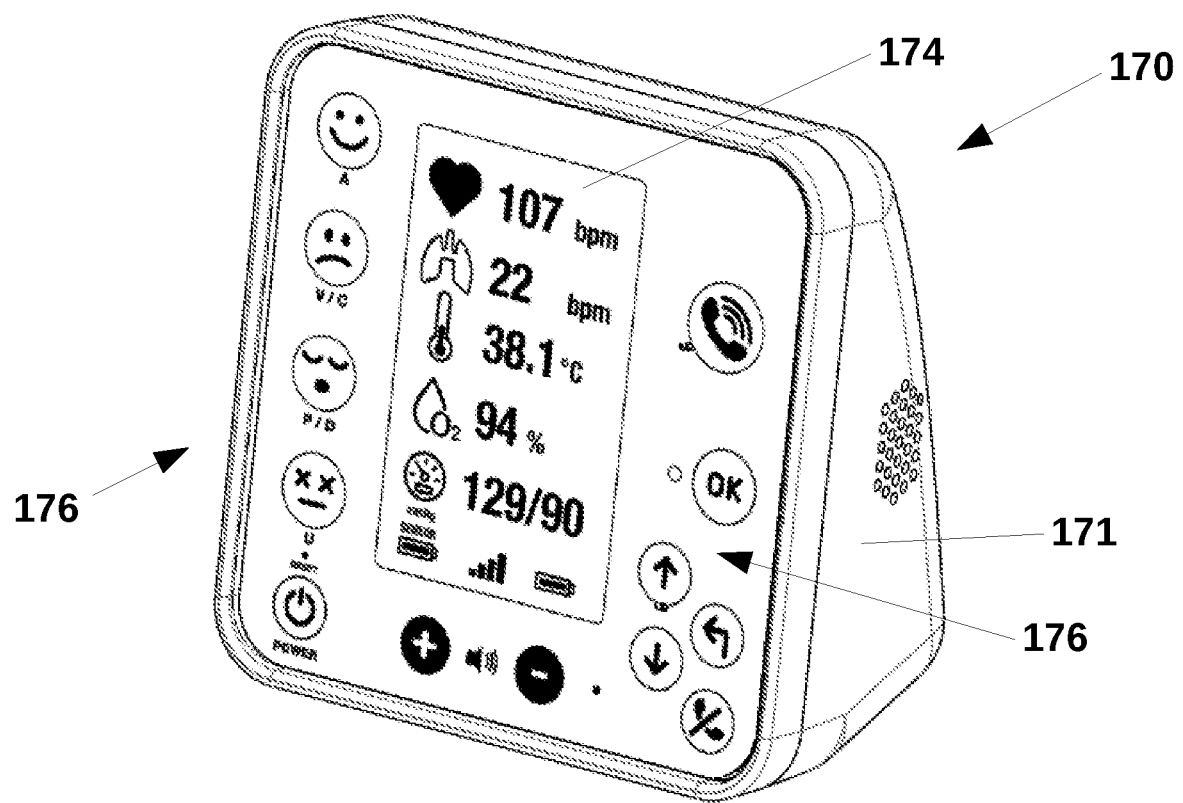
FIG. 5 is a front isometric view of a relay in accordance with one or more embodiments of the present invention.

FIG. 5 is an exploded view of a BCG sensor in accordance with one or more embodiments of the present invention.

In accordance with one or more embodiments of the present invention, wearable sensor 120 may comprise a sensor 140 in the form of ballistocardiography (BCG) sensor 142 for sensing forces related to respiration movement by patient 30. The BCG sensor 142 waveform data can be used also in the calculation of blood pressure of patient 30. The requisite extracted quantitative data obtained via BCG sensor 142 is used to calculate respiration rate, and/or respiration volume, and/or heart rate, and/or heart stroke volume, as well as or instead providing data for blood pressure calculation of patient 30.

In accordance with one or more embodiments of the present invention, BCG sensor 142 is a manufactured cellular, ferroelectret film 142a, with a permanent charge and preferably made by Emfit Oy of Finland. The elastic, cellular ferroelectret film is disposed between electrodes to form a BCG sensor and is entirely inside the enclosure 122 of wearable sensor 120. Instead of cellular ferrolelectret film, also piezoelectric PVDF film, or PZT piezoceramic sensors can be used as force sensor but as they are more sensitive to bending than direct thickness change, the structure as described is more advantageous to ferroelectret film.

In accordance with one or more embodiments of the present invention, ferroelectret film 142a comprises a laminate that is made of layers of self-biased ferroelectret film, and conductive films alternating with layers of polyester. Conductive layers disposed as the topmost and bottom most layers, i.e., exterior layers act as the ground (reference) layer and electromagnetic interference (EMI) shield. The interior conductive layers are sized smaller to prevent from protruding to or beyond any edges of laminate to avoid 50/60 Hz interference. The exterior conductive layers have the conductive film protrude to the edges of the laminate. In practice any metal, but preferably printed silver paste, or etched copper or aluminum are most suitable as the conductive material.

The width of the laminate is suitable for making a connection with printed circuit board 124. printed circuit board 124 has connection area for a signal conductive layer (small) and for a ground conductive layer. Using a conductive adhesive, and folding the tip of the laminate, both electrodes can be conveniently connected to printed circuit board 124, where the signal acquisition is on the bottom side of the laminate, i.e. the bottom-most conductive layer.

BCG sensor 142 is used for heart rate calculation during restful stay because advantageously the signal acquisition, i.e. the acquisition of measurement data, advantageously uses much less power than ECG sensor 141 or PPG sensor 143.

BCG sensor 142 importantly is capable to measure very low frequencies based on the forces generated from breathing and produce the signal for respiration rate calculation. Moreover, BCG sensor 142 provides measurement data of the ballistic movement of the heart of patient 30. Resultant extracted quantitative data are certain signal peaks for timing those with an ECG signal and/or PPG signal for the calculation of systolic blood pressure of patient 30.

Photoplethysmograph (PPG) Sensor

In accordance with one or more embodiments of the present invention, wearable sensor 120 may comprise a sensor 140 in the form of a photoplethysmograph (PPG) sensor 143 for determining pulse oximetry as extracted quantitative data by sensing blood oxygen levels with the PPG sensor 143 as measurement data.

While pulse oximetry measurement is usually taken on the index finger, or at some cases from ear lobe, such locations are generally unacceptable to obtain measurement data for healthcare management system 100 since it may interfere with the patient's daily activities or stigmatize the patient. Further, sensor placement at extremities can be problematic, such as being prone to body movements, and, thus, create movement artifacts in measurement data in the form of data that actually measures decreased blood perfusion in the case of hypothermia or trauma, limiting blood circulation, and showing delay up to 15 seconds when compared to chest measurement. Thus, PPG sensor 143 performs oximetry at consist sensor location on the chest with minimal discomfort to patient 30 and with minimal signal delay or adverse measurement sensitivity to movement from patient 30 to obtain measurement data.

PPG sensor 143 may be arranged on a supplemental printed circuit board 124 proximal to ferroelectret film 142a and may sandwich ferroelectret film 142a between printed circuit board 124 and a supplemental printed circuit board 124. A flexible connection places PPG sensor 143 in communication with supplemental printed circuit board 124. In one embodiment of the wearable sensor, one PPG sensor is arranged in the corner of the circuit board with BCG sensor 142. In some use cases it is preferred to have two PPG sensors, one in two corners of the skin side of the wearable sensor.

In the overmolding step or steps, PPG sensor 143 is disposed entirely within enclosure 122. Only its LEDs are arranged visible. The PU material of enclosure 122 is soft enough to let forces travel through and let BCG sensor 142 sense forces of heart beats and breathing as measurement data in an analog sound acquisition portion and use also as seismocardiograph (SCM) or phonocardiograph (PCG).

Therein, the special BCG sensor material is very much microphonic and has perfect acoustic impedance matching with human tissue. When ballistocardiogram (BCG) is a measurement of the recoil forces of the body in reaction to cardiac ejection of blood into the vasculature, the seismocardiogram represents the local vibrations of the chest wall in response to the heartbeat. Phonocardiograph is used for monitoring the acoustic signals generated by movement of the valves and blood flow in the heart vessels besides contraction and relaxation of the myocardium.

An analog preamplifier can be added to supplemental printed circuit board 124. The preamplifier preferably has a low pass filter that is high enough to permit heart beat sound waves to travel through the PU; for example, a low pass filter may have 100 Hz low pass filter. Moreover, BCG sensor 142 can make calculations using the measurement data of the heart rate, respiration, listening heart sounds, and listening lungs breathing sounds of patient 30 to obtain extracted quantitative data.

While BCG sensor 142 measures the recoil forces of the body of patient 30 in reaction to cardiac ejection of blood into the vasculature, the seismocardiogram (SCG) represents the local vibrations of the chest wall in response to the heartbeat. Phonocardiograph (PCG) may then be used for monitoring the acoustic signals generated by the movement of the valves and blood flow in the heart vessels besides the contraction and relaxation of the myocardium.

Healthcare monitoring system 100 may record and store all band-pass-filtered signal, i.e. extracted quantitative data, from a sensor 140 in wearable sensor 120 at a high sampling rate and output the extracted quantitative data files over an API to authorized users as .edf files.

In accordance with one or more embodiments of the present invention, the ECG sensor 141 may be integrated in the PPG sensor 143. Therein, the combined ECG sensor 141 and PPG sensor 143 is single chip. Preferably, the single chip is a MAX86150 chip from Maxim Integrated Products, which is a first-of-a kind biosensor module, comprised of internal LEDs, photodetectors and an ECG analog front-end (AFE) to advantageously provide highly accurate, FDA-certifiable PPG and ECG performance in compact, power-saving design.

To meet the IEC 60601-1 standard, the electronics diagram between hooks and other circuitry is designed suitable to be used safely also when user is being treated by AED defibrillator.

Skin Temperature Sensor

In accordance with one or more embodiments of the present invention, wearable sensor 120 may comprise a sensor 140 in the form of a skin temperature sensor 144 for measuring the skin temperature of patient 30 as measurement data to determine the core temperature, i.e. temperature of the center of the torso, of patient 30 as extracted quantitative data. Skin temperature sensor 144 may be any suitable device, but is preferably configured to be an ST Microelectronics MEMS sensor mounted on or integrated with printed circuit board 124.

Preferably, skin temperature sensor 144 is placed near to PPG sensor 143 in wearable sensor 120 and is encapsulated by the PU material of enclosure 122. If two PPG sensors is used, there may be two skin temp sensors as well. If patient 30 is sleeping non-advantageously so that wearable sensor is partially raised away from skin, then at least one end of it is against skin and always at least one PPG and one temp sensor retain in touch with skin. Additionally, the skin temperature sensor 144 is placed so that the MEMS sensor is proximal to an outer surface of the enclosure. Although, a thermal loss due to the PU from an actual skin temperature occurs, the detected measurement data is preferably calibrated (using preferably temperature calibration table) by the firmware of the MEMS sensor to be extracted quantitative data the core temperature, i.e. temperature of the center of the torso, of patient 30.

Motion and Position Sensor (Accelerometer and Gyroscope)

In accordance with one or more embodiments of the present invention, wearable sensor 120 may comprise a sensor 140 in the form of a 3-axis accelerometer and gyroscope sensor, i.e. a motion and position sensor 145 for detecting motion and make position measurement as measurement data. Motion and position sensor 145 may be any suitable device known, but is preferably a single chip such as an ST Microelectronics MEMS sensor that is mounted on or integrated with printed circuit board 124 measures motion of patient 30 relative to a prior position and state of acceleration of patient 30.

The measurement data of motion and position sensor 145, and in particular accelerometer data is used for artifact rejection of other signal sources, motion measurement and position detection. Further, certain motion patterns as obtained from extracted quantitative data of motion and position sensor 145 may be the result of tremors or palpitations. These are indicative of other strong indicators of anomalies, or in more extreme case such as epileptic seizures. In the long term, either increased or decreased activity levels may be indicators of patients worsening status. Moreover, extracted quantitative data obtained by motion and position sensor 145 may be used to augment accuracy of the respiration rate measurement.

In accordance with one or more embodiments of the present invention, motion and position sensor 145 is a single chip ST Microelectronics MEMS sensor containing 6-axis accelerometer and gyroscope.

In accordance with one or more embodiments of the present invention, motion and position sensor 145 is an integrated single MEMS sensor providing both 9-axis accelerometer and gyroscope.

Electrodermal Activity (EDA) Measurement Sensor

In accordance with one or more embodiments of the present invention, wearable sensor 120 may comprise a sensor 140 in the form of an electrodermal activity (EDA) sensor 146 for measuring electrodermal activity based on skin resistance as measurement data. Electrodermal activity varies with the state of sweat glands in the skin. In turn, sweating is controlled by the sympathetic nervous system, and skin conductance is an indication of psychological or physiological arousal.

In accordance with one or more embodiments of the present invention, to provide electrodes for EDA sensor 146, hook portions 123a fit for providing electrical contact to electrodes arranged on the chest band 150. A segment of each hook portion 123a may be used as electrical contact to an electrode in the chest band. Therein, hook portions 123a are divided into two electrically isolated sections. The slot in the chest band 150 to fit to the hooks comprise then two conductive portions and a non-conductive portion between the two conductive portions. Two electrodes on the same side (left or right) of chest band are formed so that from each a separate electrical signal can be directed to the appropriate part of signal acquisition, for example, one for ECG and one for EDA.

In accordance with one or more embodiments of the present invention, when only single lead ECG is used in wearable sensor 120, the chest band 150 comprises two electrodes 150a and 150b, disposed on opposite sides, one on the left and one on the right side, of the chest band 150. In one embodiment, both left and right sides can have two electrodes, i.e. four in total and arranged in the chest band. Then, by having also one electrode arranged on the enclosure 122, a total of 5 electrodes can be arranged such that they are comfortable to the patient 30, and provide a re-usable sensor for monitoring one or two lead ECG, and even EDA.

Chest Band

In accordance with one or more embodiments of the present invention, healthcare management system 100 may comprise a chest band 150 having any suitable dimension and any suitable material. However, preferably chest band 150 is made of a fabric, is formed as a chest strap that is re-useable, and can be employed with ECG electrodes 150a, 150b with the electrodes of ECG sensor 141. An adjustment buckle 150c is provided in the chest band to adjust the tightness of the chest band. Advantageously, chest band 150 allows a sufficient tight fit for the ferroelectret sensor to sense force changes and act better as phonocardiograph and seismograph.

In accordance with one or more embodiments of the present invention, the fabric of chest band 150 is a functional high-tech textile material, commonly used in sportswear.

Functional high-tech textile material is very comfortable for patient 30 and is fast-dry material providing improved user comfort and is economical. The fast-dry material instead is beneficial not only for improving the user comfort, but it helps to prevent the bacteria growth, as the humidity on the surface, provides the fertile soil for bacteria to grow.

Advantageously, chest band 150 made from functional high-tech textile material allows a sufficient tight fit for the BCG sensor 142 to sense force changes and act as a phonocardiograph and seismograph.

In accordance with one or more embodiments of the present invention, healthcare management system 100 may be configured to provide to each patient 30 several chest bands 150 for use, in case one gets wet by sweating or using sensor in shower, which is not needed as chest band 150 is easy to remove by patient 30 or caregiver 40 for showering of patient 30.

In accordance with one or more embodiments of the present invention, chest band 150 is reusable and preferably uses one or more conductive fabrics materials to define ECG electrodes 150a, 150b with the electrodes of ECG sensor 141.

Therein, ECG electrodes 150a, 150b are disposed near the opposite ends of chest band 150 and come into contact with skin of patient 30 and can be arranged to have electrically well conductive fabric. The conductive fabric is arranged to come in contact with hook portions 123a in the sensor ends. Those hooks then are mechanically and galvanically connected to printed circuit board 124.

Charge Pad

In accordance with one or more embodiments of the present invention, healthcare management system 100 comprises a charge pad using inductive charging for charging the power source of wearable sensor 120 and/or relay 170. the charge pad comprises an inductive Qi-standard charging coil on the same charge pad that is used for relay device. Wearable sensor 120 and relay 170 are carefully designed together to complement each other.

Therein, each respective power source is a rechargeable battery and the charge pad is preferably a Qi-standard charge pad. Advantageously, Qi-standard charge pads are low cost as most smart phones use this wireless charging method and are widely integrated.

Relay

FIG. 5 is a front isometric view of a relay in accordance with one or more embodiments of the present invention.

In accordance with one or more embodiments of the present invention, healthcare management system 100 comprises a relay 170 associated with one or more wearable sensors 120.

Therein, relay 170 is located in care setting 50 proximal to patient 30. For example, the location may be the home of patient 30, the room of the nursing home or rehabilitation center where patient 30 is permanently or temporarily residing.

Although a single relay 170 is described here as being functionally associated, i.e. used, with one wearable sensor 120 worn by a single patient 30, one relay 170 may be used with multiple wearable sensors 120, each of which is worn by one respective patient 30. Conversely, more than one relay 170 may be used with one wearable sensor 120 worn by a single patient to give a patient 30 the ability to roam freely yet be close to assistance via healthcare management system 100. In fact, more than one relay 170 may be used with more than one wearable sensor 120, each worn by a single patient 30, to give a plurality of patients 30 the ability to roam freely yet be close to assistance via healthcare management system 100.

In accordance with one or more embodiments of the present invention, relay 170 comprises any suitable shape. A relay enclosure 171 is configured to provide structural stability and structural integrity to relay 170 and defines the shape of relay 170. The relay enclosure 171 houses and/or secures a computing device for data processing and communications, a power source, a display 174, and a user interface 176.

Relay enclosure 171 preferably has an inclined front surface for ease of viewing of display 174 and access of user interface 176. The inclined front surface cause the shape of relay 170 to be a triangular shape in cross-section. The inclined front surface is configured to be partially used on one lateral portion by display 174 and on another lateral portion by user interface 176.

Communications Telephony

In accordance with one or more embodiments of the present invention, relay 170 includes a communications telephony, which may be any suitable means including internet telephone, VOIP data call, or any other communications method that places patient 30 and/or caregiver 40 in at least voice communications with healthcare team 45.

Preferably, relay 170 comprises a cellular network RF module for use on one or more cellular telephone networks, i.e. mobile telephone networks, since such cellular telephone networks have a high reliability, widespread coverage, low power consumption, and are readily networkable into other devices.

Preferably, the cellular network RF module for relay 170 is Gemalto GmbH flagship 3G cellular network module, EHS6-A. It is the 5th generation of Gemalto's Java embedded machine-to-machine (M2M) modules and has a simplified highly efficient, end-to-end industrial communication including high quality analog audio, Java ME 3.2 client runtime platform optimized for resource-constrained M2M applications. It significantly reduces total cost of ownership (TCO) and time to market by sharing internal resources such as memory, a large existing code base and proven software building blocks.

Therein, the ultra-compact hardware design incorporates minimal power consumption and an extended product life-cycle to guarantee long product availability. Advantageously, the extended security concept with the latest TLS/SSL engine of relay 170 provides highly secure and reliable TCP/IP connectivity with healthcare clinical system 200 in a cloud or server installation. Enriched internal flash file system enables firmware updates to relay 170 and wearable sensor 120 over-the-air (FOTA) when required. Sophisticated sandbox modeling and layered architectures simplify device management (DM) and separate mobile network operator approvals from application code development, allowing simultaneous progress of both phases for a shorter time to market.

If relay 170 for any reason cannot push the data to healthcare clinical system 200, a buffer memory in relay 170, and/or in sensor, holds extracted quantitative data until a connection is restored. No data is deleted in either wearable sensor 120 or relay 170 before it is safely stored in the healthcare clinical system 200 and healthcare clinical system 200 has confirmed such storage.

Moreover, as known in the art, cellular network RF modules readily include an integrated global positioning system (GPS). Preferably, the cellular network RF GPS module for relay 170 is an Antenova GPS/GNSS RF Module M10578-A3 simple, drop-in GPS or GNSS receiver solution, which provides an advantageously small size and an advantageously low current consumption.

A GPS location for relay 170 is advantageous for locating patient 30 since when in use, patient 30 is expected to wear wearable sensor 120 at all times and when patient 30 leaves their home for any purpose, for example to go shopping, to take relay 170 with them. Thus, when patient 30 is in distress, the integrated GPS can determine a position of relay 170 and advise healthcare team 45 via the cellular network with the expectation that patient 30 is at the same or nearby location.

To effect voice call, between patient 30 and/or caregiver 40 and healthcare team 45, relay 170 includes a microphone, i.e. preferably an analog microphone or digital chip microphone, and speaker to be used as known in the art and is operatively connected to the cellular network RF module. In turn, the cellular network RF module is operatively connected to the printed circuit board 124.

Relay 170 and wearable sensor 120 each preferably comprises a Bluetooth (BT5) wireless module from manufacturer Fanstel Corp., USA for, preferably, encrypted communication between wearable sensor 120 and relay 170 at a range of up to 210 meters. The wearable sensor circuitry includes a buffer memory large enough to collect at least 24 hours of extracted quantitative data.

With the Bluetooth (BT5) chipset the relay may be used as a hub for more than one wearable sensor 120, or for other devices and permit incorporating data from third party devices, such as weight scales, spirometers, glucometers, and the like to further the health of patient 30.

Therein, Bluetooth (BT5) chipset provides support for NFC-tag. Advantageously, out-of-Band (OOB) pairing using NFC simplifies authenticated pairing between two Bluetooth devices by exchanging authentication information over an NFC link. Thus, a relay 170 and a wearable sensor 120 can be paired in an IT environment before the system is physically deployed to patient 30 in a busy care setting 50 and reduces the stress on healthcare team 45 who allocate hardware to patients.

Relay 170 preferably use a rechargeable Li-ion battery with 2500 mAh capacity as a power source and of used continuously for data transfer from wearable sensor 120 to the cloud provides a lifespan between charging of 3-6 calendar days, depending on how good a network connection is, how many voice calls are is used, and how often relay 170 checks its location via GPS. The power source of relay 170 is charged using the charge pad, or by plugging it into for example power supply with USB-C connector, or can have both methods.

Display

In accordance with one or more embodiments of the present invention, relay 170 comprises a display 174 for viewing one or more extracted quantitative data determined wearable sensor 120.

Display 174 is preferably configured to utilize only a portion of a front surface of relay enclosure 171, i.e. the inclined front surface. While display 174 may any suitable display, and, preferably has very high-resolution capability for graphic images, high contrast for good indoor/outdoor readability, is viewable in any light from edge-of-vision darkness to brightest sunlight, and has wide/symmetrical viewing angle.

In accordance with one or more embodiments of the present invention, display 174 preferably is a small, lighted, LCD display and in particular a SHARP Memory LCD display, which is readily available and requires only $\frac{1}{40} \sim \frac{1}{80}$ of a standard liquid-crystal-display power consumption and only $\frac{1}{1000}$ of an AM-TFT LCD's power consumption, and has excellent reflective display performance.

User Interface

In accordance with one or more embodiments of the present invention, relay 170 comprises a user interface 176 for use by patient 30 and/or caregiver 40 to select suitable answer to questions, i.e. an inquiry event or clinical event, raised by an AI-engine in the cloud, i.e. provide qualitative data, and for making a call to nurse at central monitoring station when needed.

To obtain qualitative data, relay 170 includes user interface 176 that allows patient 30 and/or caregiver 40 (especially an informal caregiver 40) to communicate with healthcare team 45, i.e. to communicate a clinical event. User interface 176 allows entry of qualitative data, e.g., pain and well-being scores.

Advantageously, patient inputs of qualitative data are critical for many reasons, not least because respiration, blood pressure and consciousness are probably the three most important parameters. Moreover, standard monitoring devices cannot measure consciousness. However, response by patient 30 to questions or instructions can tell caregiver 40 and/or healthcare team 45 how well the brain of patient 30 is functioning and ultimately reducing death and disability from undetected deterioration, while providing a 'safety net' to high-risk patients after discharge to their home.

Additionally, user interface 176 allows patient 30 to express himself that they are thirsty (perhaps dehydrated), light-headed or faint (altered neurological or cardiovascular function), nauseous (neurological or gastrointestinal dysfunction), in pain, or simply "feeling well" or "unwell."

In accordance with one or more embodiments of the present invention, user interface 176 is a virtual interface and wherein display 174 is a touch sensitive display extended across the front surface of relay enclosure 171.

In accordance with one or more embodiments of the present invention, user interface 176 preferably shares the front surface of relay enclosure 171 with display 174 and user interface 176 comprises one or more capacitive interface keys operatively mounted to or in the front surface of relay enclosure 171.

In accordance with one or more embodiments of the present invention, user interface 176 preferably shares the front surface of relay enclosure 171 with display 174 and user interface 176 comprises one or more interface keys having a haptic feedback, i.e. keys having tactile switches, and that are mounted to or in the front surface of relay enclosure 171. Therein, keys with switches that provide an haptic feedback serve certain patient populations better than capacitive keys; for example, such as a teenager with epilepsy.

In accordance with one or more embodiments of the present invention, interface keys 176*a* may be a key for initiating a voice call via one or more predetermined phone numbers and/or data voice call, a plurality of keys for volume adjustment, and one or more keys to indicate and/or select a response which will be used as qualitative data. The one or more keys to indicate and/or select a response may also be used to make selections on display 174.

Method of Obtaining Vital Signs from Measurement Data

Figure 6:
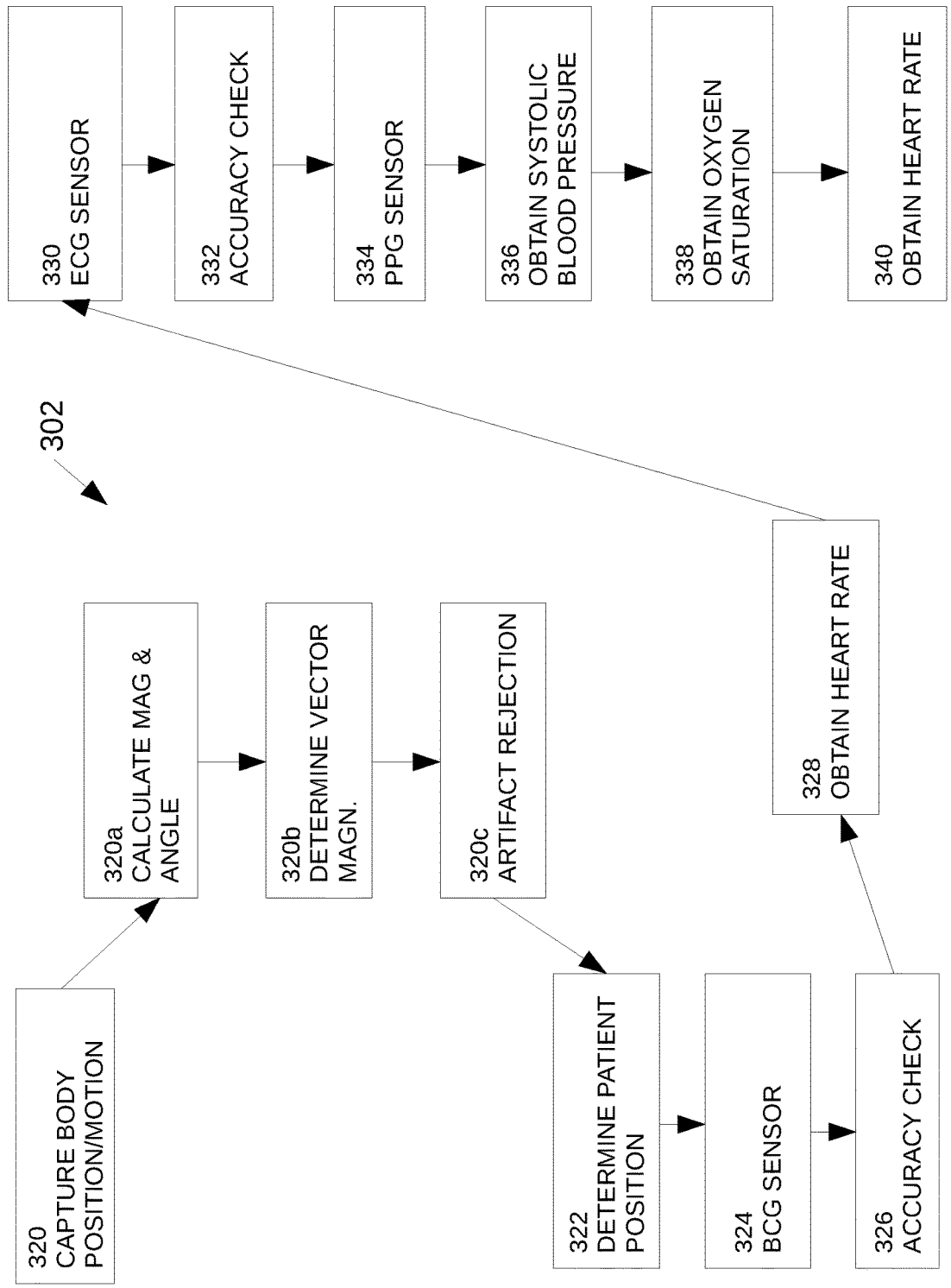
FIG. 6 is a schematic view of a method obtaining vital signals using measurement data of one or more sensors of wearable sensor 120 in accordance with one or more embodiments of the present invention.
Figure 7:
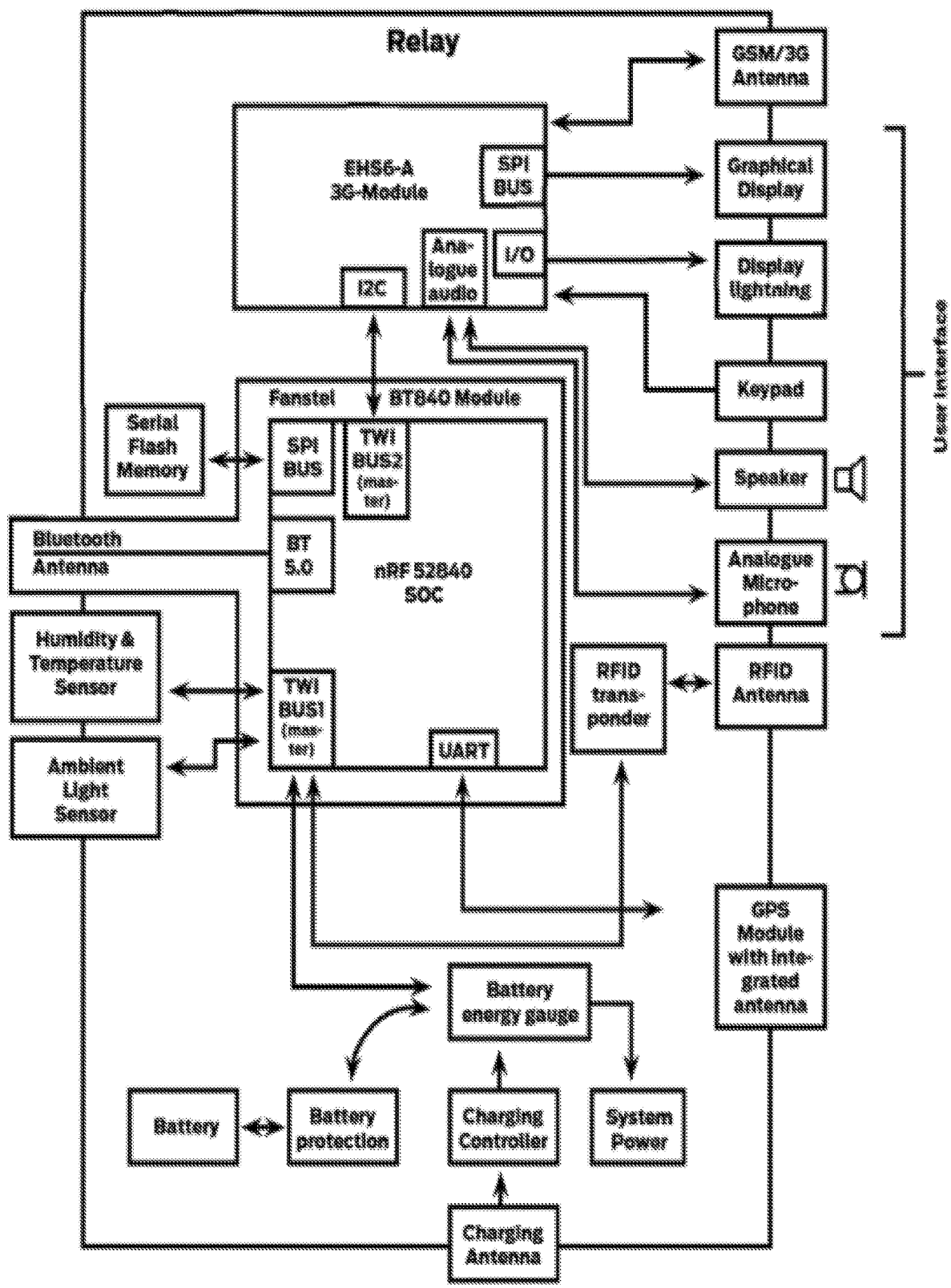
FIG. 7 is a schematic view of a relay in accordance with one or more embodiments of the present invention.

FIG. 6 is a schematic view of a method obtaining vital signals using measurement data of one or more sensors of wearable sensor 120 in accordance with one or more embodiments of the present invention.

In accordance with one or more embodiments of the present invention, wearable sensor 120 uses patient monitoring software 300 on printed circuit board 124 to execute a method 302 to obtain vital signs from one or more measurement data of sensors 140.

Advantageously, patient monitoring software 300 aims to minimize consumption optimization of power source 125 by determining how to use the one or more sensors 140 efficiently. Wearable sensor 120 includes three different sensors 140, i.e. ECG sensor 141, BCG sensor 142, PPG sensor 143, for monitoring the heart rate of patient 30 and four different sensors 140, i.e. ECG sensor 141, BCG sensor 142, PPG sensor 143, and motion and position sensor 145, for capturing the breathing (respiratory) rate as measurement data.

In accordance with one or more embodiments of the present invention, patient monitoring software 300 executes a method 302 to monitor the heart and breathing (respiratory) rate of patient 30.

In accordance with one or more embodiments of the present invention, patient monitoring software 300 to capture the heart and breathing (respiratory) rate of patient 30 as measurement data according to a predetermined schedule that may be time based, adjusted for an estimated schedule of the patient based on likely physical activity, or determined in any other suitable way.

Using a predetermined schedule, permits printed circuit board 124 to reduce power consumption from power source 125. Moreover, patient monitoring software 300 optimizes the use of sensors 140, specifically ECG sensor 141, BCG sensor 142, or PPG sensor 143, to achieve the highest accuracy of measurement data and lowest possible power consumption from power source 125.

In accordance with one or more embodiments of the present invention, a predetermined schedule for executing method 302, measuring for vital signs, is a 2 minute interval if patient 30 is in professional care setting 50, such as a hospital. However, healthcare team 45 can change the interval manually to 8 minutes, or it can change automatically when patient 30 relocates to an informal care setting 50 such as their home.

In accordance with one or more embodiments of the present invention, the predetermined schedule may be changed by patient monitoring software 300 by determining that a location, obtained from GPS data, is not in its approved table of professional care settings 50 and assuming that patient 30 has been released from the professional care setting 50.

In accordance with one or more embodiments of the present invention, method 302 schedules a heart rate measurement at an interval that is more frequent than determination of other vital signs. That is, method 302 engages in a split interval having a first scheduled part for heart rate measurement and a second scheduled part with a less frequent interval for measurement of the heart rate and the other vital signs.

In a first step 320 of method 302, patient monitoring software 300 wakes motion and position sensor 145 to capture the body position and motion status of patient 30 as measurement data by obtaining signals from the accelerometer and the gyroscope. Therein, step 320 (physical status check step performs a plurality of algorithms. In a substep 320a, a first algorithm calculates the position from the three-dimensional accelerometer signal by calculating the magnitude and angle of the gravity vector (accelerometer set) in two planes: the transverse plane (y-z) to estimate toll (left side, supine, right side, prone) and sagittal plane (x-z) to estimate pitch (up, supine, down, prone). The plane with the higher magnitude vector is chosen. The quadrant where the vector points determines the position.

In subsequent substep 320b, a second algorithm calculates activity by determining the vector magnitude of a 3D signal and band-pass filters it to 0.5-7 Hz. The second algorithm uses an integral to calculate an activity count from the three-dimensional accelerometer signal based on integral method activity measurement. That is, a magnitude vector is determined and an integral of the magnitude vector is calculated in a 5 seconds moving window.

In subsequent substep 320c, an artifact rejection may be considered by having healthcare team 45 verify with patient 30 one or more anomalies found substeps 320a and/or 320b and optimize the many physical situations that patient 30 finds himself in. For example, patient 30 can be resting, sitting, talking, walking, jogging, or traveling in a car on a bumpy road.

In a subsequent step 322, patient monitoring software 300 determines by analyzing measurement data from step 320 if patient 30 is resting, sitting, or standing but not talking.

In a subsequent step 324, if patient 30 is resting, sitting, or standing but not talking, patient monitoring software 300 wakes BCG sensor 142 and instructs BCG sensor 142 to use ferroelectret film 142a to capture the heart rate and breathing (respiratory) rate of patient 30 as one or more measurement data.

In a subsequent step 326 (verification step), patient monitoring software 300 determines if measurement data is related to the heart rate is accurate.

If patient monitoring software 300 determines in step 326 that measurement data related to the heart rate is accurate, in a subsequent step 328, patient monitoring software 300 calculates extracted quantitative data from measurement data obtained from the BCG sensor 142 and uses the extracted quantitative data as the heart rate.

Since BCG sensor 142 uses consumes less power from power source 125 than ECG sensor 141, method 302 advantageously extends the usable life of wearable sensor 120 between charges. That is if BCG sensor 142 obtains a heart rate for patient 30, method 300 returns to an idle state after completing the first scheduled part and measurements from the other sensors 140 are not taken.

If patient monitoring software 300 determines in step 326 that measurement data related to the heart rate is inaccurate, in a subsequent step 330, patient monitoring software 300 wakes ECG sensor 141 and instructs ECG sensor 141 to capture the heart rate of patient 30, and if the both ECG and PPG are one SoC, take also oxygen saturation as one or more measurement data. As part of step 330, patient monitoring software 300 calculates extracted quantitative data from measurement data obtained from the ECG sensor 141.

ECG sensor signal acquisition is at least started, preferably, once per hour to obtain waveform data for blood pressure calculation. In movement artifact occasions too, the ECG based heart rate calculation may be started more often.

In a verification step 332, patient monitoring software 300 determines if measurement data related to the heart rate is accurate by comparing extracted quantitative data from measurement data obtained by BCG sensor 142 and extracted quantitative data from measurement data obtained by ECG sensor 141. If the extracted quantitative data differ from each other, patient monitoring software 300 uses the ECG based extracted quantitative data as the heart rate. If the extracted quantitative data from both provide same the value, the output value can be flagged as "very" accurate.

If patient monitoring software 300 determines in step 332 that measurement data related to the heart rate is inaccurate (because for example ECG sensor 141 had poor contact with the skin of patient 30), in a subsequent step 332, patient monitoring software 300 wakes PPG sensor 143 and instructs PPG sensor 143 to capture the heart rate and breathing (respiratory) rate of patient 30 as well as the blood oxygen saturation as one or more measurement data. The patient monitoring software 300 then uses measurement data obtained by PPG sensor 143 to determine extracted quantitative data, which is the heart rate of patient 30.

A subsequent step 334 is used to determine the breathing (respiratory) rate. Therein, patient monitoring software 300 filters measurement data from BCG sensor 142 at a very low band between 0.07-1.00 Hz when step 320 indicated movement of the chest of patient 30 and determines the extracted quantitative data, which is the breathing (respiratory) rate.

If measurement data from the BCG sensor is unclear, extracted quantitative data related to breathing (respiratory) rate is obtained from ECG sensor 141 and corroborated by the extracted quantitative data from BCG sensor 142 or PPG sensor 143. If corroboration is not possible, accelerator data from motion and position sensor 145 is used by patient monitoring software 300 to determine the breathing (respiratory) rate.

In a step 336, patient monitoring software 300 uses measurement data obtained by ECG sensor 141 and the measurement data in a signal band between 6-16 Hz from BCG sensor 142 to determine extracted quantitative data that is the systolic blood pressure. Alternatively, patient monitoring software 300 may use peaks of the measurement data date from ECG sensor 141 and BCG sensor 142 to determine the systolic blood pressure or, more preferably, utilizing peaks of the measurement data date from ECG sensor 141 and PPG sensor 143 to determine the systolic blood pressure.

In a step 338, patient monitoring software 300 determines oxygen saturation levels, i.e. SpO2, using measurement data obtained by PPG sensor 143 by being arranged against the skin of patient 30. To minimize power consumption, step 338 is performed as a second scheduled part, and, for example, only on an hourly basis.

In a step 340, patient monitoring software 300 determines the heart rate variability (HRV) physiological variation in the time intervals between individual heartbeats, i.e. variation of beat-to-beat intervals. HRV can be used to estimate stress level and give other useful information about patient.

Therein, patient monitoring software 300 used measurement data from the ECG sensor 141, which is clear for machine peak detection algorithm, to identify intervals between individual heart beats. The measurement data is managed by using an RMSSD (Root Mean Square of the Successive Differences, successive differences being here neighboring RR intervals) with a standard window of 3 minutes to obtain extracted quantitative data, which is the HRV. To minimize power consumption, step 340 is performed as a second scheduled part, and, for example, only on an hourly basis.

Healthcare Clinical System

Referring to FIG. 1, in accordance with one or more embodiments of the present invention, healthcare management system 100 comprises a healthcare clinical system 200 that is, preferably, deployed in a professional care setting 50, for example a hospital, and used by or in association with healthcare team 45.

Preferably, healthcare clinical system 200 includes a plurality of subsystems to advantageously serve patient 30. Therein, healthcare clinical system 200 comprises a patient database 202, a message queue subsystem 204, a notifications and messages service subsystem 205, SMS service subsystem 206, an email service subsystem 207, a data and events communications subsystem 210 for communicating with one or more wearable sensor 120 and/or one or more relays 170, and a healthcare analysis subsystem 220 using an artificial analysis (AI) engine 222 and an artificial intelligence (AI) factory 224 for improving accuracy and reducing the number of false alarm events.

Patient Database

Patient database 202 provides persistent storage for data for all components of healthcare clinical system 200. For safety, reliability, and performance, patient database 202 preferably is a multi-node server cluster. Therefore, a lost of single instance does not prevent usage of software stack and compromise patient safety.

Database server cluster is used to achieve high availability and throughput for database service that will store all data application stack needs and processes. Inside the database cluster multiple techniques are used to ensure performance and safety needs, including replication, multipathing for network and storage connections, and automated fail-over with fault detection.

Message Queue Subsystem

Message queue subsystem 204 is used to deliver messages to different parts of a healthcare management system 100 and provides asynchronous communication so that the sender and receiver are not forced to interact at the same time. The messages are stored and persisted in a queue until a consumer at the other end of the queue processes them. Storage is preferably accomplished on queue database 204a.

If healthcare management system 100, healthcare clinical system 200, or another part of the healthcare management system 100 fail and message delivery is not possible failure or heavy load makes delivery difficult, message queue subsystem 204 instruct that the messages are stored until the system or relevant parts of the system are functional again. To improve scalability more consumers can be added to process the queues faster.

Using a message queue subsystem 204 is beneficial for decoupling different services in the system and for the scalability of the system. In this particular system it transmits messages between services and database.

Notifications and Messages Service Subsystem

Notifications and messages service subsystem 205, i.e. handler, is important since communications between patient 30 and healthcare team 45 is an important aspect of healthcare management system 100 and healthcare clinical system 200. Subsystem 205 ensures that relevant parts of healthcare management system 100 that use artificial intelligence can notice worsened condition and generate questions (for example GCS Glasgow Coma Scale) to check on the condition of patient 30.

Moreover subsystem 205 ensures that messages find their way to healthcare team 45 and formal caregivers 40. There can be Android and iOS Apps for nurses and other supervisors who are to monitor that patient deterioration are acted on. There can be apps also for formal caregivers and patients to receive not so vital messages. It is possible that some hospital customer prefer only to use SMS method for these messages that are not crucial. In short, this service handles SMS, email and Android/iOS push notifications.

SMS Service Subsystem

SMS service subsystem 206, i.e. push notification and messages services subsystem, provides user access authorizations to participants of healthcare management system 100 and sends artificial intelligence generated messages.

Email Service Subsystem

Email service subsystem 207 provides various messages and notifications to participants of healthcare management system 100, for example from monitoring services to IT admins.

Data and Events Communications Subsystem

Preferably, healthcare clinical system 200 comprises a data and events communications subsystem 210, i.e. DE subsystem 210, which in turn comprises a data and events communications (DE) software executing on a computing device, i.e. a server, deployed at care setting 50 and accessible by one or more authorized users of healthcare team 45 to communicate with one or more wearable sensor 120 and/or one or more relays 170 used by one or more patients 30 for an inquiry event, clinical event, and/or alarm event. For clarity, one patient 30 using a single wearable sensor 120 and a single relay 170 associated with patient 30 are described herein.

Wearable sensor 120 and relay 170 can initiate a connection with DE subsystem 210 via any suitable network. However, preferably, as described herein, wearable sensor 120 communicates with relay 170 via Bluetooth and relay 170 communicates with DE subsystem 210 via a cellular network. Thus, patient 30 and/or wearable sensor 120 can initiate connection to DE subsystem 210 via relay 170 and/or relay 170 can initiate a connection to DE subsystem 210 via cellular network. Healthcare clinical system 200 can initiate a connection with this software for an inquiry event, a clinical event and/or an alarm event, interchangeably "a patient event." The connection is used to receive data and patient events from relay 170 or directly from wearable sensor 120 if wearable sensor 120 includes a cellular network capable LTE-M/NB-IoT communications module.

When DE subsystem 210 receives vital signs information and extracted quantitative data from a sensor, DE software 202 decrypts the received data and forwards it to a database storage. For security, data allocation, and/or authentication, DE subsystem 210 comprises a table of a metadata information of all the devices, i.e. wearable sensor 120 and/or relay 170, that are configured to connect to the specific DE subsystem 210. The metadata includes the serial numbers, connection statuses, "last seen alive" timestamps. and other information that is required to maintain a large number of simultaneous device connections as is known in the art. Each device connectable to a DE subsystem 210 is individually authenticated and a foreign entity (bogus or hacked device, any unknown server etc.) will not be able to connect.

While preferably the DE software and/or DE subsystem 210 are each optimized for performance, DE subsystem 210 can also be scaled across multiple servers when the number of connectable devices exceed the limitations of the hardware. As is known in the art, software and hardware tools may be allow server status monitoring to maintain service availability.

Preferably, the DE software comprises a user interface for configuring and managing connected devices, viewing data, inquiry events, clinical events, and alarm events, i.e. patient events using a browser-based Web User Interface (WUI) for ease of use and management.

Healthcare Analysis Subsystem

Healthcare clinical system 200 comprises a healthcare analysis subsystem 220 that in turn comprises an artificial analysis (AI) engine 222 and an artificial intelligence (AI) factory 224 for improving accuracy of the healthcare clinical system 200 and for reducing the number of false alarm events.

A high accuracy and low number of false alarm events are a priority healthcare clinical system 200. Thus, healthcare analysis subsystem 220 gathers data over time to further improve the accuracy of the clinical analysis modules running in healthcare management system 100.

AI engine 222 comprises one or more clinical analysis modules for analyzing one or more physiological and/or medical conditions of patient 30 and executes the respective clinical analysis modules. The goal of healthcare management system 100 and more particularly the goal of healthcare clinical system 200 is to detect a wide variety of causes of physiological and/or medical conditions, area, subject, filed, or subfield ranging from general deterioration to specific ones such as sepsis. AI engine 222 is configured such that physiological and/or medical conditions are evaluated by an independent analysis module within the AI engine 222.

Clinical analysis modules may be:
automated EWS system (with individually adjustable thresholds)
utilizing data merely from system
deterioration detection as anomaly detection, based on k-NN approach
data from system and EMR (lab results)
deterioration detection based on deep neural networks
data from system and EMR (lab results)
diagnosing selected life threatening condition (e.g. sepsis, internal bleeding, etc) based on deep neural networks
data from system and EMR (lab results)

The modularity of AI engine 222 provides extreme flexibility in allowing the creation of highly specified modules for each physiological and/or medical conditions. Clinical analysis modules may be created specific to each center/hospital where software system is running. With a minimal setup, only generic deterioration module (in simplest form like automated NEWS score) may be utilized, whereas in some larger hospitals several, even highly complex analysis modules can be running in AI engine 222 at the same time. Some of the modules may be specialized in recognizing deterioration, whereas other clinical analysis modules may be responsible for diagnosing rare condition.

Each clinical analysis module comprises a learned algorithm, which has learned behavior of suitable data to detect certain physiological and/or medical conditions, such as deterioration or sepsis. That is, each clinical analysis module specializing, directed to, expert in a predetermined physiological and/or medical area, condition, subject, field, or subfield and each clinical analysis module analyzes the healthcare data of patient 30 with a learned algorithm to detect physiological and/or medical conditions specific to that area, subject, field, or subfield to advise healthcare team 45. To permit integration in AI engine 222, each clinical analysis module has defined software interfaces both for incoming and outgoing data, such as incoming healthcare data and outgoing processed data, making it easy to integrate the respective module into AI engine 222. A software interface provides constants, data types, types of procedures, exception specifications, and method signatures, and where needed public variables, to make software integration easier. A software interface is also used to define an abstract type that contains no data but defines behaviors as method signatures. A class having code and data for all the methods corresponding to that interface and declaring so is said to implement that interface.

Therein, AI factory 224 is a subsystem of healthcare analysis subsystem 220 and executes on the server an artificial intelligence learning program in the background of the healthcare analysis subsystem 220 and/or healthcare clinical system 200. AI factory 224 is responsible for automatic evolution, using a generic algorithm, of the clinical analysis modules and incorporating new data into one or more of the clinical analysis modules, tweaking one or more model parameters and feature selections, and executing one or more learning phases. Once a better performing clinical analysis module is created, AI factory 224 replaces the older clinical analysis module of AI engine 222 with the improved clinical analysis modules. Also, third party clinical analysis modules may be injected to AI factory 224 to compete with existing modules, or to augment them, and if quality suffices, and become a clinical analysis modules in AI engine 222.

The artificial intelligence learning program learns over time from feedback of healthcare team 45. Each time a patient event, and especially an alarm event occurs, healthcare team 45 is requested to report whether that patient event was correct or not. Additional learning by the artificial intelligence learning program occurs when healthcare team 45 reports deteriorations of patient 30 that were not noticed by healthcare clinical system 200 or healthcare management system 100. The feedback can be directly used for self-learning by healthcare analysis subsystem 220 and reduces false patient event significantly.

One important part of AI Engine is to interface with analysis modules to offer well functioning data streams, suitably formatted from system and also from hospital EMR system. Further, data from analysis is sent out to same systems.

Because the AI factory 224 utilizes a multitude of machine learning approaches, the AI engine 222 can improve its performance as the patient cases accumulate. Initially there are not much training data available and it accumulates over time, the AI engine 222 can be divided into three phases based on how data driven algorithms it can use.

At initial phase the techniques that work with no or limited data are deployed. Subsequently, when the first batches of training data have accumulated a set of popular machine learning algorithms can be introduced. The new techniques will be introduced as rogue contenders and thus need to compete against the current roster of algorithms. This guarantees that healthcare clinical system 200 is not biased towards any particular technique. Finally, when extensive amount of data are available, deep learning techniques can be applied.

The following techniques are part of the base algorithms:
1. Early phase—limited/no training data
   a. Meta-analysis, expert knowledge and early warning score derived rule-based systems that are implemented as decision trees
   b. Anomaly detection based on k-Nearest Neighbour algorithm
2. Middle phase—a few batches of training data
   a. Logistic regression—a common method to calculate various medical scores
   b. Support vector machines
   c. Random forests
   d. Neural networks
   e. Bayesian network
3. Last phase—extensive amount of training data
   a. Convolutional neural networks
   b. Autoencoder neural networks Learning algorithms use features derived from a patient record, which can contain information shown below:

| id | Name | Short | Source | type |
|---|---|---|---|---|
| 1 | Heart rate | HR | Wearable sensor | Numerical time series |
| 2 | Heart rate variability | HRV | Wearable sensor | Numerical time series |
| 3 | Respiration rate | RR | Wearable sensor | Numerical time series |
| 4 | Blood pressure | BP | Wearable sensor | Numerical time series |
| 5 | Oxygen saturation | SpO2 | Wearable sensor | Numerical time series |
| 6 | Activity | Act | Wearable sensor | Numerical time series |
| 7 | Position | Pos | Wearable sensor | Categorical |
| 8 | Temperature | T | Wearable sensor | Numerical time series |
| 9 | Glascow come scale | GCW | Relay UI or WUI | Numerical |
| 10 | Age | A | EMR | Numerical |
| 11 | Gender | G | EMR | Categorical |
| 12 | Reason of hospitalization | RoH | EMR | Categorical |
| 13 | Operation | Op | EMR | Categorical |
| 14 | Date of ICU release | ICUr | EMR | Numerical |
| 15 | Date of hospital release | Hor | EMR | Numerical |
| 16 | Sodium | Na | EMR | Numerical time series |
| 17 | Potassium | K | EMR | Numerical time series |
| 18 | Hemoglobin | Hb | EMR | Numerical time series |
| 19 | Glucose | Gluc | EMR | Numerical time series |
| 20 | Hematocrit | HCT | EMR | Numerical time series |
| 21 | Creatine | Crea | EMR | Numerical time series |
| 22 | Bicarbonite | Bicar | EMR | Numerical time series |
| 23 | White blood cell count | WBC | EMR | Numerical time series |
| 25 | Lactate | Lac | EMR | Numerical time series |
| 26 | Blood urea nitrogen | BUN | EMR | Numerical time series |

Above is outlined the complete path to create self learning system for detecting patient deterioration.

Algorithms & AI/Machine Learning Software

The mathematical computation of AI service may be implemented with Matlab 2018a (MathWorks, Inc., Natick, Mass., United States, 2018). Other languages and software such as Golang or Python for example are possible. Matlab's Statistics and Machine Learning Toolbox and Neural Network Toolbox have implementations and training algorithms for decision trees (fitctree), k-nearest neighbors (fitcknn), support vector machines (fitcsvm), random forests (TreeBagger), logistic regression (mnrfit), neural networks (fitnet, train), convolution neural networks (trainNetwork) and autoencoder networks (trainAutoencoder). Third party feature selection toolbox FEAST may be implemented. Functions for Bayesian network structure optimization and fitting can be implemented. Optimization of algorithm parameters can be done using both open source and proprietary variants of well known global optimization algorithms such as differential evolution and genetic algorithm. Several feature functions that calculate time series trends etc. from vital signs can be constructed.

AI Service

The data analysis system is designed as a platform, which consists of, comprises, or includes inward and outward data streams, and different detection/analysis modules in the middle. Platform design allows to design different analysis/detection modules in most efficient way, by choosing for each module only those input variables that are needed to detect that particular way of deterioration or physiological malfunction. This method is opposing to a design where all different anomalies are incorporated in to single detection module, which would probably lead to severely bloated module with poor performance. Further, platform design allows third parties to develop their own detection/analysis modules with their best resources and understanding, leading to improved overall performance, and allowing also commercial incentive to those parties who develop useful modules.

Modular design allows also deployment of the system in different configurations to different customer segments (as example hospital with general ward patients, left ventricular hypertrophy (LVH) patients, COPD patients, people severe epilepsy, elderly care, athletes etc), meaning that only those detection modules are utilized that are necessary. For example, there may be modular units that are specialized in such cases, which are seen only very rarely, or never at usual wards, and thus it would be unnecessary to use modules capable to detect some extremely rare anomaly in general wards.

Inward data streams to AI Service, consumed by analysis modules, may be of different complexity levels:
1. variables measured by the sensor itself,
2. additional information provided by WUI or relay users (level of consciousness, functional status and other structured nursing observations such as restlessness, sleepiness/sedation, dyspnea, sweating, nurse worry, etc),
3. numerical information available from hospital's electronic medical record system (EMR), such as laboratory results (blood urea nitrogen, white blood cell count, glucose, platelet count, hemoglobin, creatinine, calcium, etc),
4. more complex information from EMR, data in text format such as doctors observations, diagnoses, prescriptions and clinical notes,
5. binary data such as imaging results or other biosignal traces (ECG, EEG EMG etc).

Analysis modules have essentially three different tasks, in order of increasing complexity: to identify general deterioration, to diagnose adverse conditions, and suggest/optimize treatments.

Thus, output data from ENS system can be roughly divided in to three classes:
1) notifications/alarms about onset/oncoming patient deterioration,
2) diagnoses of several life threatening conditions (sepsis, upper airway obstruction, internal bleeding, etc.),
3) suggestions for treatments, procedures or medication dosing.

Information in classes 1 and 2 can be represented as a binary variable ("all ok", or "deterioration detected"), discrete variable ("safe", "observe", "warning" and "urgent") or as a score, i.e. as integer ranging from 0 to 100.

Integration with Electronic Medical Records System/Electronics Health Records System (EMR/EHR)

In healthcare management system 100 and/or healthcare clinical system 200 a Push/Get API is provided and today hospital IT systems require it shall be compliant with FHIR standard. It is provided to exchange data between hospital electronic medical record (EMR) system and system. There are detailed instructions from base documentation to jurisdiction for third-party developers in the current officially released version of FHIR standard published by HL7. FHIR describes data formats and elements as resources and the resource consists of, comprises, or includes a URL, a metadata, a human-readable XHTML summary, a set of defined data elements like a different set for each type of resource and an extensibility framework to support variation in healthcare. In this innovation context the data transmission from the aspect of observation is one important. For an example when the system solution takes laboratory results into account for deterioration analysis the format of the resource is important.

Calculating PTT for Blood Pressure

Figure 10:
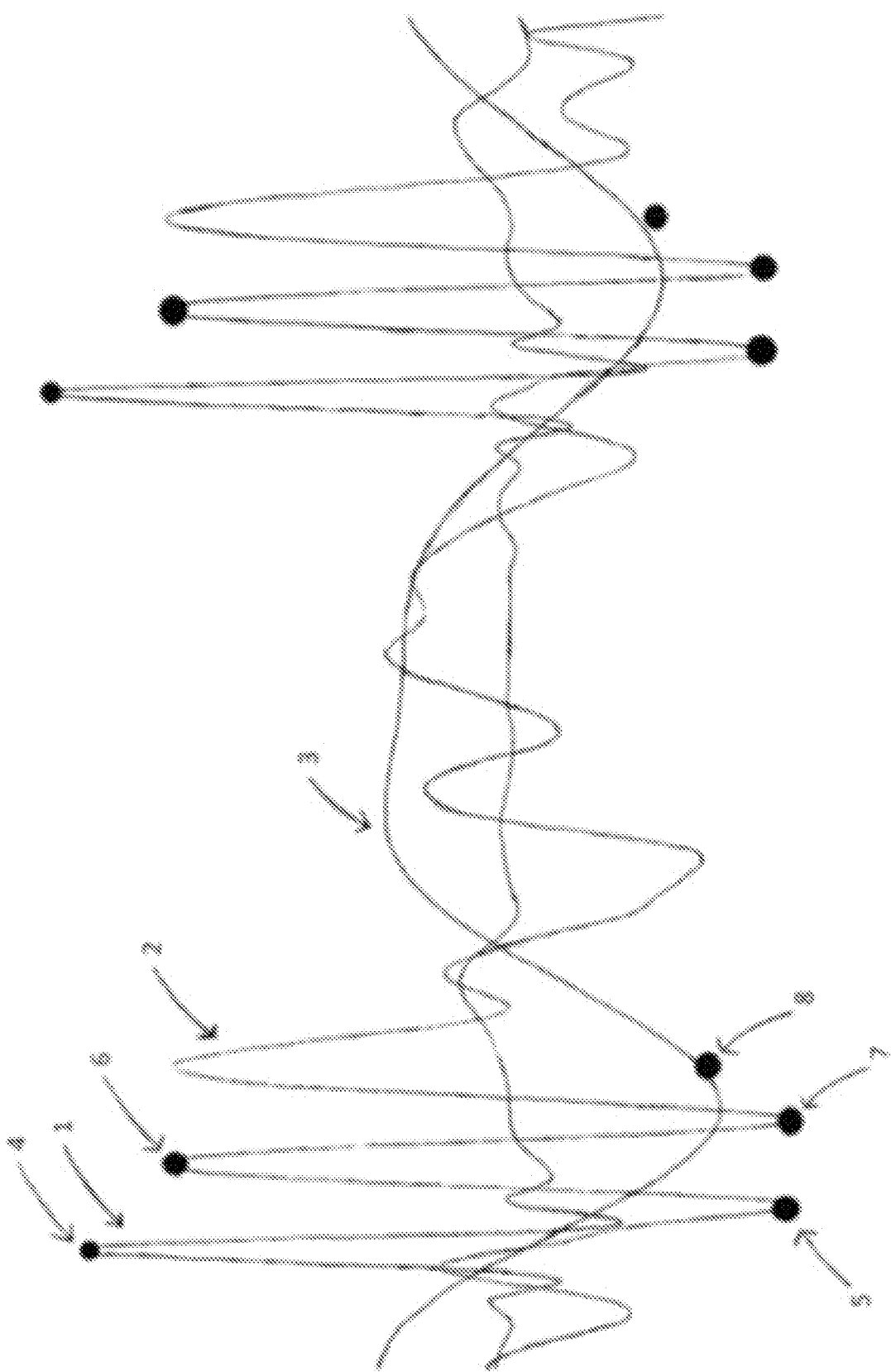
FIG. 10 is an exemplary diagram of measurement data from a wearable sensor in accordance with one or more embodiments of the present invention.

Referring to FIG. 10, PTT is the time between two pulse waves propagating on the same cardiac cycle from two separate arterial sites. It's a well-known relationship between PTT and blood pressure (BP).

FIG. 10 shows actual footage measurement data from wearable sensor of the innovation. Filtered and scaled ECG (1), BCG (2) and PPG (3) signals. ECG R peaks (4), BCG I (5), J (6) and K (7) peaks and PPG P points (8) respectively.

When BP is high, it's takes less time from ECG R peak (referring to FIG. 10, peak number 4) wave to PPG valley (referring to FIG. 10, point number 8) and when BP is low, it's takes more time from ECG R wave peak to PPG valley respectively. When PTT is measured as the time delay between ECG R peaks and corresponding points in the PPG (photoplethysmogram) pulse waves it's called PAT (pulse arrival time). PAT which includes the cardiac PEP (pre-ejection period) has been proposed as a surrogate of PTT. In order to get real PTT value, the PEP must be subtracted from PAT. To do that, the BCG sensor 140 made of cellular ferroelectret self biased film can be used. When J-peak (referring to FIG. 10, peak number 6) is detected from the BCG signal, the PEP can be calculated from the time interval between the ECG R peaks and BCG J peaks.

To calculate the PAT, the proper points of PPG valley must be detected. PPG valleys is minimally impacted by wave reflection and that's why it's better to use the PPG valleys instead of PPG peaks. To find preferred point from PPG valleys sensor use intersecting tangents method because it's produced great precision for cardiac periods compared with ECG.

Since the wearable sensor of innovation can measure the correct PTT value, it can measure the aortic PWV (pulse wave velocity) value when the distance traveled by the pulse wave is known. PWV can tell about the condition and stiffness of the arteries. The best site for measuring PWV is located in the aorta because relationship between PWV and BP is the highest in central elastic arteries.

Figure 11:
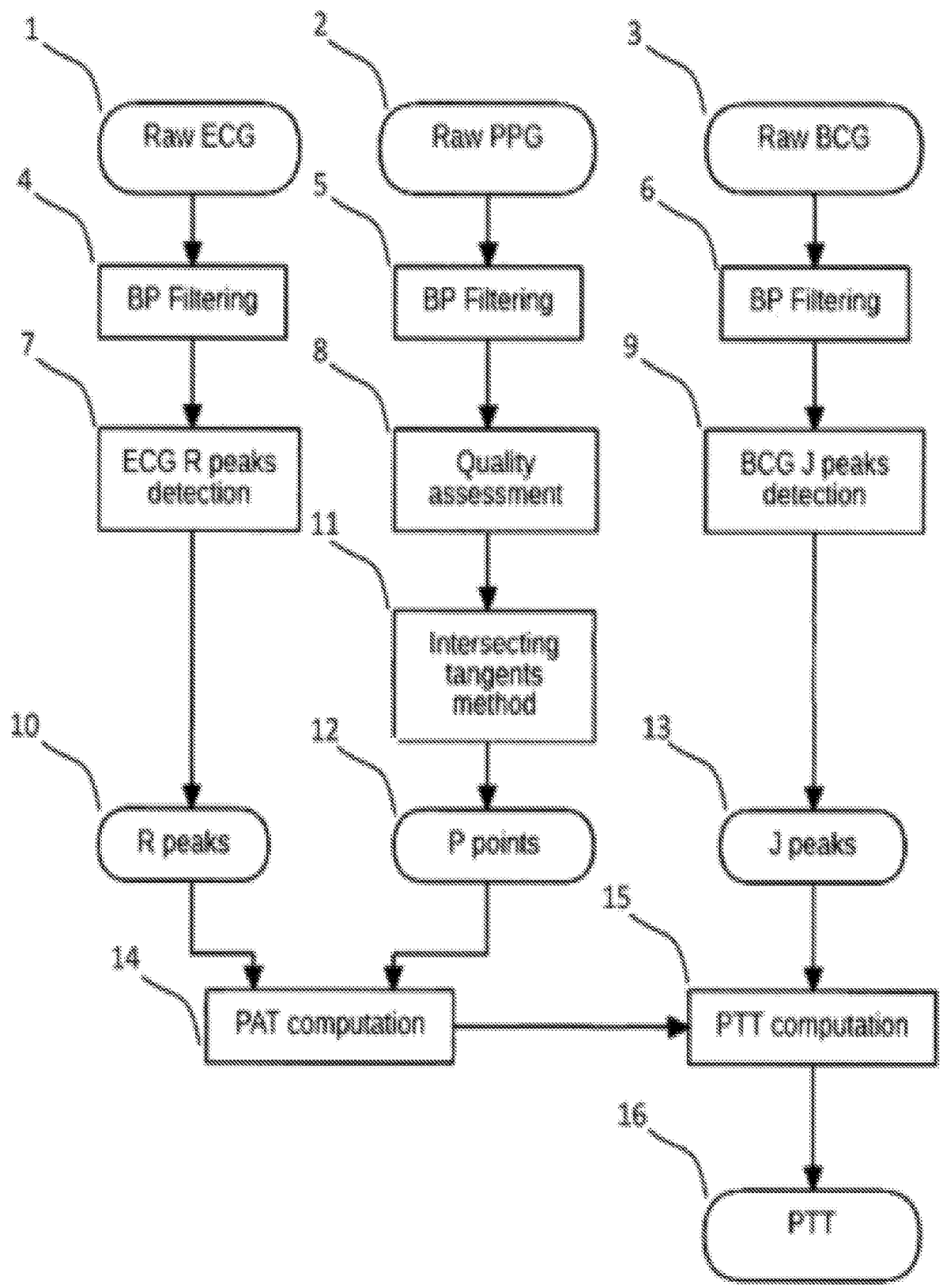
FIG. 11 is a schematic view of a data analysis method in accordance with one or more embodiments of the present invention.

Referring to FIG. 11, outline of the PTT (pulse transit time) calculation algorithm 2) Input: Raw ECG signal (1), raw PPG signal (2) and raw BCG signal (3).
3) Bandpass filtering of raw ECG (4), PPG (5) and BCG (6) signals.
4) Remove physiological artefacts e.g. respiration.
5) Remove moving artefacts.
6) Remove DC and high frequency artefacts.
7) ECG R peaks detection (7).
8) PPG P points detection by using detected ECG R peaks.
9) PPG signal quality assessment (8).
10) Remove outliers.
11) P points detection (12) by using intersecting tangents method (11).
12) Find maximum of $1^{st}$ derivative of PPG signal from predefined window.
13) Find zero point of $1^{st}$ derivative of PPG signal from predefined window.
14) Draw tangents line through the found derivative points.
15) Find points of intersection of the tangent lines.
16) PAT computation (14) by using detected R peaks and P points.
17) Subtracting the corresponding value of R peaks from value of P points.

18) PTT computation (15) by using detected J peaks (9, 13)

19) Subtracting the corresponding value of R peaks from value of J peaks.

20) Subtracting the previous value from value of PAT.

21) Output: calculated PTT values (16).

PTT Algorithm Results

When using raw ECG, raw PPG and raw BCG data from sensor as an input to PTT algorithm, wearable sensor can give PTT value from output which is proportional to BP. By using PTT information sensor can monitor blood pressure trend changes in hypertensive or hypotensive episodes occurring in patients. FIG. 10 shows actual data from signal processing. PTT algorithm to sensor raw signal data. Line with number 1 in the main picture is ECG and line with number 2 is PPG respectively. Dots number 3 in picture are R peaks and dots with number 4 are the corresponding P points. Smaller picture illustrates intersecting tangents method used to find P point from PPG during one cardiac cycle.

Data Analysis System for Detecting Patient Deterioration
System Data Analysis

Figure 9:
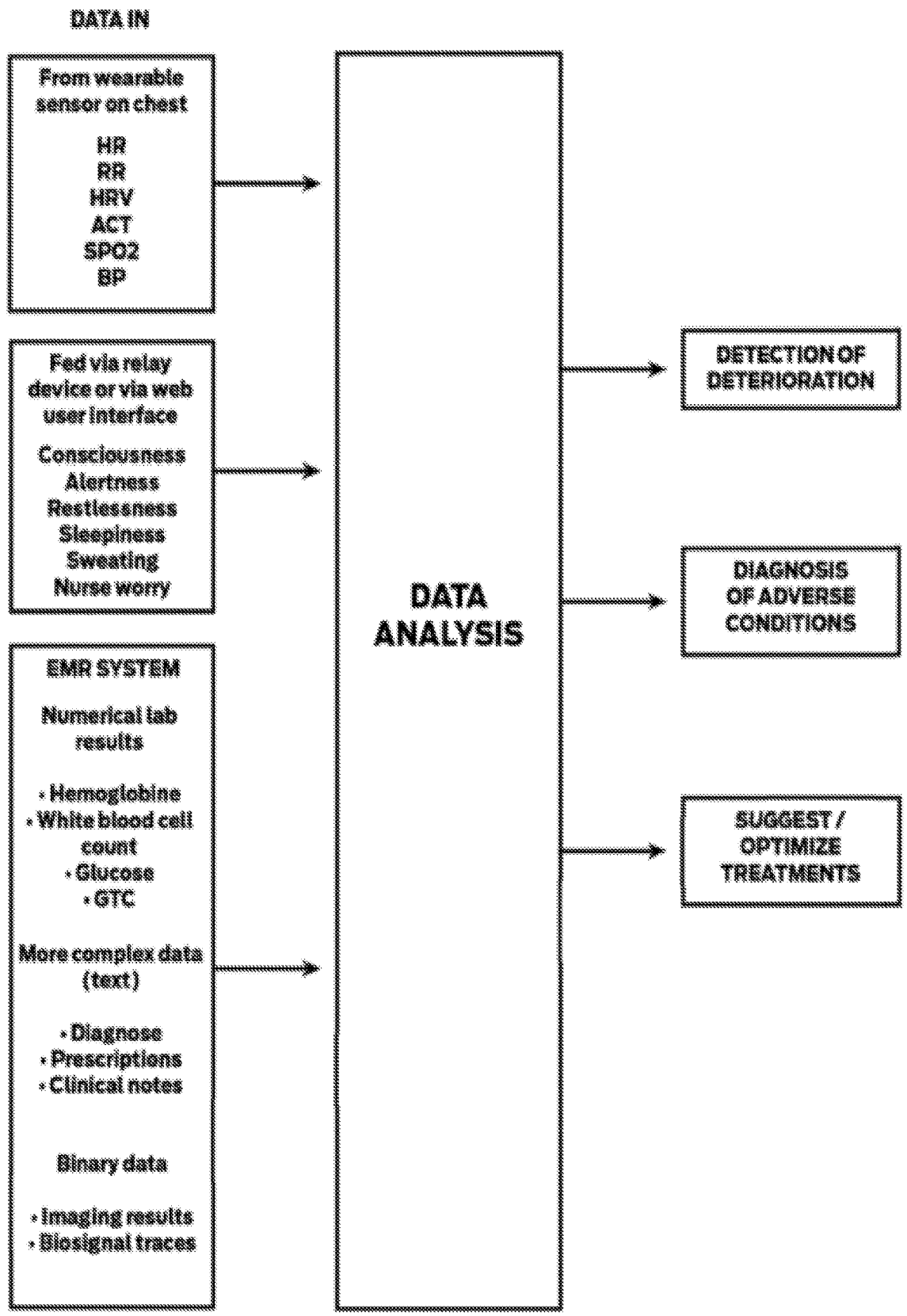
FIG. 9 is a schematic view of a data analysis method in accordance with one or more embodiments of the present invention.

Analysis system consists of, comprises, or includes several separate parts (FIG. 9). With regard to data, the system can get data from the sensor heart & breathing (respiratory) rate, heart rate variability, blood pressure, oxygen saturation, skin temperature, posture and activity levels; as user input from relay or via web interface (level of consciousness, functional status and other structured nursing observations such as restlessness, sleepiness/sedation, dyspnea, sweating, nurse worry, etc), and also from EMR system (laboratory results, demographics, clinical notes, prescriptions, imaging results, etc).

Data from different sources is consumed by data analysis modules, which have three main objectives for processing the data (given here in order of increasing complexity):
to identify general deterioration,
to diagnose different kinds of adverse conditions, and
suggest/optimize treatments.

Referring to FIG. 9, general overview of system data analysis structure. At left are shown different inbound datastreams, which are analyzed, and different level of information is produced as an output.

In most rudimentary level deterioration can be detected by simply automatizing so called NEWS ("National Early Warning Score") scoring system, using data provided by the wearable sensor, and setting suitable threshold for score to trigger alarm. This approach is not always optimal, because all patients are individuals, with their own baseline values for heart and breathing (respiratory) rates etc., and also with their own medical history, and fitness level. Thus, same scoring and threshold may lead to excessive amount of false alarms, or maybe even missed alarms.

In a more advanced setting deterioration can be detected using sophisticated data analysis and so called machine learning algorithms, which are able to learn behavior of some phenomenon from the data, or recognize hidden patterns in data without specifically being programmed to do so. These methods make possible to detect general deterioration without knowing reason to it, or to diagnose certain physiological problems. Intelligent algorithms may also find relevant parameters to predict some adverse event, i.e. they may identify antecedent changes prior to adverse events in such parameters, which may not be obvious to human analyst. In this sense, machine learning and artificial intelligence can be used to achieve three objectives outlined above.

Machine learning approaches have two main categories: supervised learning, and unsupervised learning. In supervised learning there must be such data available where input parameter values and corresponding output value(s) are given, data is thus annotated or labeled. In unsupervised learning output value is not given, and aim is to find unknown clusters in the data or estimate probability density function of the data. Based on the type of the output value, approaches can be further divided into regression, where output has continuous values, and classification, where output is finite set of discrete categories.

To create a successful machine-learning platform the following issues need to be addressed:
1) the general model (i.e. algorithm) selection problem,
2) the structure and hyper parameter optimization of the selected model,
3) feature selection (which variables are used in analysis) and
4) the model fitting (i.e. learning).

The feature selection, and data preprocessing may have large impact on the performance. The available amount of training data has also an impact in model selection. Some techniques can be deployed using only expert knowledge and some require significant amount of data. The generation of deterioration alarms need to address the nurse and informal caretaker alarm fatigue and thus high positive predictive value is crucial for the system practicality although it typically comes with expense of sensitivity.

With above considerations the system is based on multiple separate detection/analysis modules which can predict different deterioration types. To enhance accuracy and reliability, if necessary, modules can utilize ensemble averaging, where several different ML algorithms are ran within single module, and results are combined as an ensemble.

Because not tied only into one technique the AI system can optimize the general model selection problem. It can start with simpler base algorithms and introduce more data driven techniques later when the system has collected more data. AI Factory can give a (semi)automatic way to improve and update the analysis modules so that algorithms are replaced with better ones if the new ones are performing better. This way each evolution cycle produces at least as good expected performance as the previous generation. Extensive feature bank covers a wide variety of representations from EMR data to vital trends until more data driven models with representation learning capability can be utilized.

Diagnostics and Suggestions for Treatment

As can be seen in other discussions herein, even detecting deterioration without establishing cause for it can be somewhat complex task. Modules responsible for meeting objective 2, i.e. diagnosing conditions such as internal bleeding, opioid respiratory depression etc. can be implemented on similar fashion as supervised deterioration detection, although it may be required to use more complex algorithms, and/or preprocessing of data. It has been shown that deriving other features from basic measurements such as heart rate or respiration rate may greatly improve detection accuracy of algorithms. These features such as mean, median, skewness, curtosis, approximate entropy, regularity can be computed within one data series (e.g. heart rate) or features such as linear correlation, coherence, non-linear regression and synchronization between two time series' (e.g. heart rate and breathing (respiratory) rate). It has been found that performance using only basic measurements was quite poor, but with augmented features performance was greatly enhanced.

Meeting requirements for suggestions for treatments, procedures or medication dosing can be based on modules already meeting objective above, which may be simply supplemented with commonly known and accepted procedures to treat that particular condition or checklists of actions to be taken. In more complex setting, artificial intelligence data mining approach can be used to extract best treatment outcomes for particular conditions based on data stored in EMR database.

Medication dosing optimization can be performed by making small, safe (within limits) changes to dosage, and gathering data from ENS and EMR systems to deduce what was the outcome of that particular dosing. This data can be utilized for meta-modeling, i.e. to create regression model (such as artificial neural network or radial basis function) about dose-response-data, and run optimization algorithm on meta-model to find optimal value, i.e. dosing that produces the best response. This process can be run iteratively, and accumulated data can be utilized for other people being in similar situation.

AI System Architecture

Figure 12A:
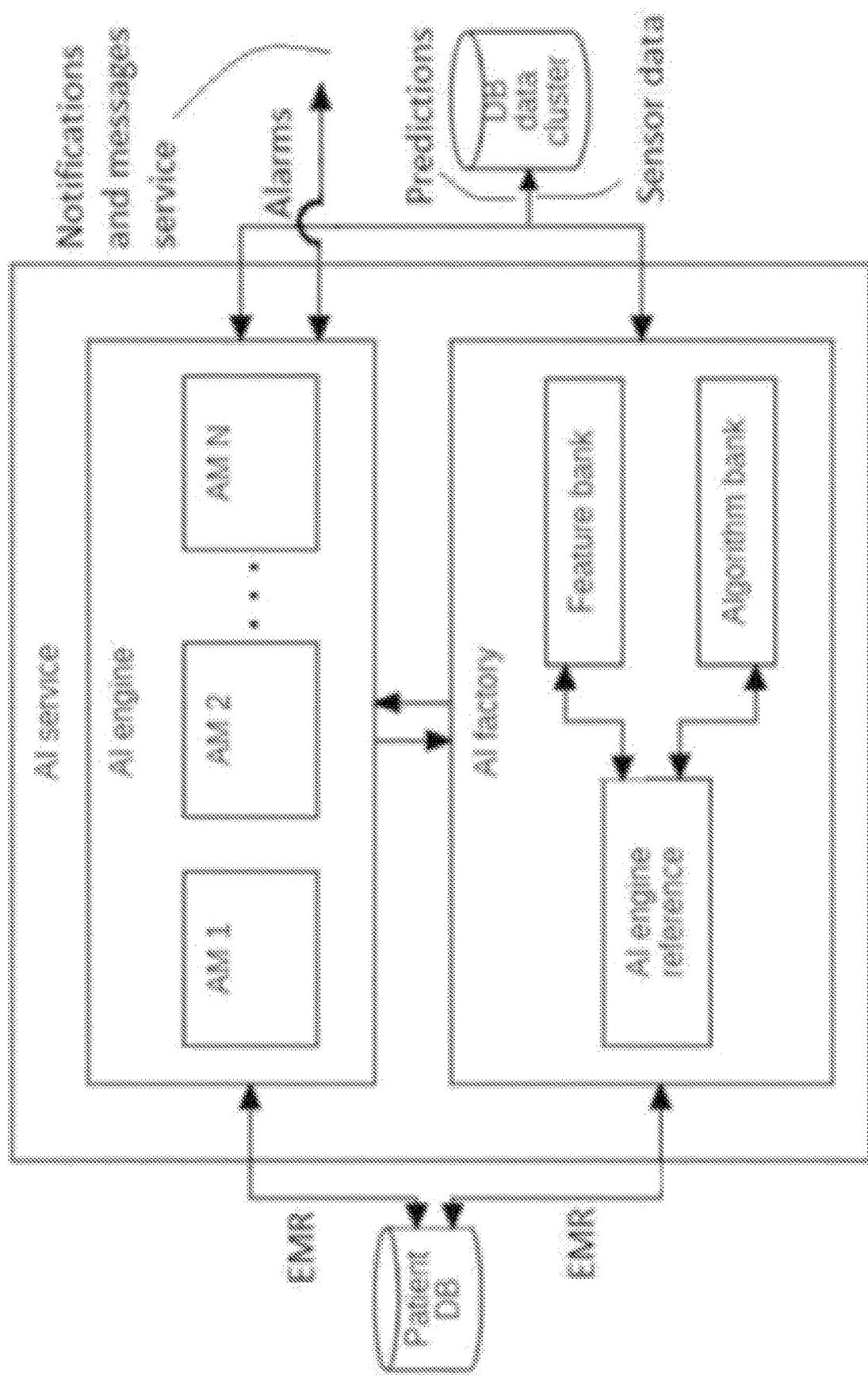
FIG. 12a is a schematic view of an AI service module in accordance with an embodiment of the present invention.
Figure 12B:
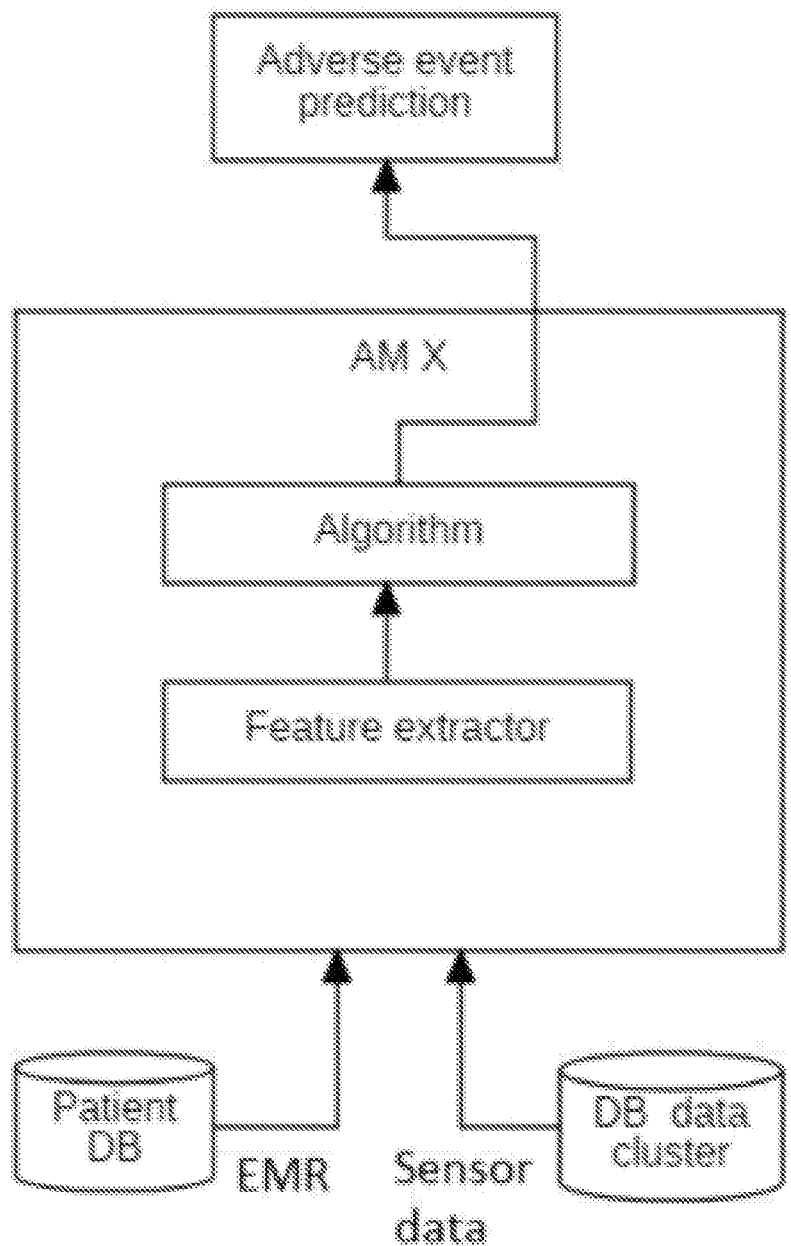
FIG. 12b is a schematic view of AI service module wherein different adverse events are predicted by specialized analysis modules in accordance with one or more embodiments of the present invention.

FIG. 12a is a schematic view of an AI service module in accordance with an embodiment of the present invention, FIG. 12b is a schematic view of AI service module wherein different adverse events are predicted by specialized analysis modules in accordance with one or more embodiments of the present invention.

Figure 8:
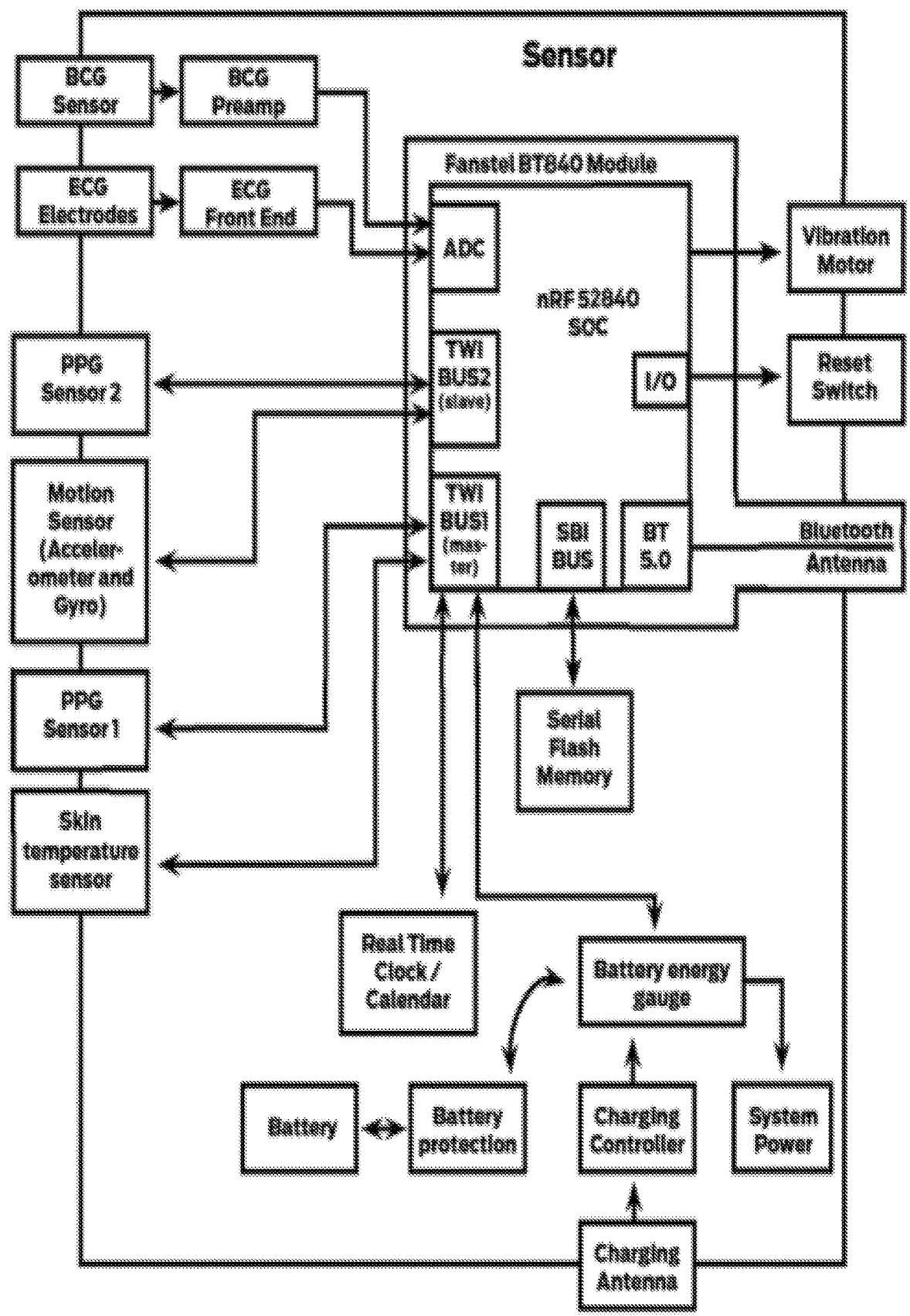
FIG. 8 is a schematic view of a wearable sensor in accordance with one or more embodiments of the present invention.

The system AI service module is divided into two main components; AI Engine and AI Factory, see FIG. 8 for an overview. The AI Engine provides the high-throughput online deterioration detection and diagnostics for patients under surveillance. The improvement of existing modules (i.e. performing the learning phase for the model with augmented or most recent data) and creation/validation of new modules is separated to its own entity, AI Factory, so that computationally demanding and time consuming module improvement does not intervene with the normal surveillance/detection routine. AI Factory may be implemented on its own dedicated server.

AI Engine

FIG. 12a shows an overview of the system AI service module. (A) The module consists of, comprises, or includes AI Engine that observes patients and predicts/detects their deterioration using Analysis Modules (AM) and AI Factory which builds new analysis modules and refines old ones, as shown for example FIG. 12b. (B) Different adverse events are predicted by specialized analysis modules. Module has a feature extractor which selects the relevant patient data and also performs representation transformations e.g. calculates trends from vital signs.

The AI Engine runs one or more of Analysis Modules (AM), which independently predict different adverse events. See FIG. 11 for more detailed structure of an AM unit. Module can be based on any of the algorithms from AI Factory and it makes a prediction for an adverse event. In addition to a ML algorithm itself each module also has a feature extractor submodule or module that selects the relevant patient data and performs necessary transformations (FIG. 12b).

The AI Factory handles the learning and updating of Analysis Modules. It keeps a reference of the production versions of AM's currently available to AI Engine and constantly optimizes modules with regard to their parameters and newly accumulated data. AI Factory also has a collection of base algorithms and available features (data fields), that it can utilize when creating a new analysis module.

AI Factory

Optimization of performance of analysis modules is the task of the AI Factory. In the core of AI Factory is base set of machine learning algorithms, such as artificial neural network, support vector machines, logistic regression, etc. If there is a need to create new analysis module to detect or diagnose certain condition, it is possible when there is enough learning data available for that particular diagnosis. Amount of data provided for learning may not be known beforehand, but can be judged after training by deciding whether module performance is sufficient or not.

When creating a new analysis module, some or all algorithms of the base set are harnessed to task, allowed to perform feature selection or perform on human preselected features, and run series of learning iterations in order to optimize algorithm's parameters. Finally, best performing algorithm is selected as representative analysis module for that diagnosis.

In case of already existing modules new data is accumulating in to system, making it possible to further refine detection accuracy. To this end, AI Factory is configured to perform update runs after certain amount of new data for certain diagnostic task has accumulated. Another trigger for update run is introduction of new algorithm in to AI Factory's base set. If update run produces model (learned algorithm) performing better than current analysis module, that module is updated using predefined protocol, considering possible legal bindings.

It can be seen that update/optimization task for analysis modules has two dimensions: first is to optimize performance of certain algorithm on certain data by adjusting parameters and structure of that particular algorithm. Second one is similar to first one, but adding this time newly accumulated learning data. AI Factory runs first task for all or the set that is most promising algorithms in the background to the extent that allocated resources for AI Factory server allow. Thus, analysis modules can be improved, and even algorithm can be changed as time passes even if new data is not introduced.

Obviously, larger leaps in performance are to be expected when large amount of new learning data is accumulated. In the case of new data, well performing algorithm specific parameter sets from history may be utilized as starting point.

Criterion to judge performance is based on sensitivity and specificity, and can be measured for example by AUROC (area under receiver operating characteristic curve) values.

Continuous optimization is an important feature because, as discussed earlier, in initial release there is a lack of training data which excludes the applicability of data driven machine learning techniques. At early stage the analysis module need to be based on meta-analysis, expert knowledge or outlier detectors. After the system has accumulated more data, data driven analysis modules can be introduced into the system.

Each analysis module is modified so that the output is a score value, which is then transformed into a percentage that approximates the possibility for an adverse event. The final result is discretized into four categories which are more human interpretable; safe, observe, warning and urgent.

What is claimed is:

1. A healthcare management system for a healthcare team caring for a patient to serve a healthcare need of the patient, the healthcare management system comprising:
   a wearable sensor worn by the patient for obtaining healthcare data from the patient;

a healthcare clinical system comprising a healthcare analysis subsystem for analyzing the healthcare data; and a relay device in communication selectively with the wearable sensor and the healthcare clinical system;

wherein the healthcare analysis subsystem comprises an artificial intelligence (AI) engine, the AI engine comprising a plurality of clinical analysis modules, each clinical analysis module directed to a respective predetermined medical area, the respective clinical analysis module analyzing the healthcare data with a respective learned algorithm directed to the respective predetermined medical area;

wherein each clinical analysis module comprises the respective learned algorithm and a feature extractor submodule for selecting a data subset from the healthcare data and for performing data transformations from the data subset, the data subset related to the respective predetermined medical area of the clinical analysis module;

wherein each clinical analysis module of the plurality of clinical analysis modules is functionally independent of the AI engine for analyzing the healthcare data, and wherein each clinical analysis module comprises software interfaces for incoming healthcare data and outgoing processed data to integrate the respective clinical analysis module into the AI engine.

2. The healthcare management system of claim 1, further comprising an artificial intelligence (AI) factory for automatic evolution of the plurality of clinical analysis modules, the AI factory replacing an existing clinical analysis module of the plurality of clinical analysis modules with a new clinical analysis module comprising a new model parameter directed to the respective predetermined medical area.

3. The healthcare management system of claim 2, wherein the AI factory comprises
a feature bank comprising a plurality of features, and
an algorithm bank comprising a plurality of base algorithms, both adapted for creating a new clinical analysis module.

4. The healthcare management system of claim 1, further comprising an artificial intelligence (AI) factory for automatic evolution of the plurality of clinical analysis modules, the AI factory replacing an existing clinical analysis module of the plurality of clinical analysis modules with a new clinical analysis module causing fewer false alarms when serving the healthcare need of the patient.

5. The healthcare management system of claim 1,
further comprising an artificial intelligence (AI) factory for automatic evolution of the plurality of clinical analysis modules,
wherein the relay forwards an alarm even related to the healthcare data of the patient to the healthcare clinical system; and
wherein the AI factory comprises an artificial intelligence learning program learning from a feedback of healthcare team relative to an accuracy of the alarm event.

6. The healthcare management system of claim 1, further comprising an electronic medical record system, the electronic medical record system comprising laboratory results related to the healthcare need of the patient.

7. The healthcare management system of claim 1, wherein in each clinical analysis module the feature extractor submodule selects relevant healthcare data to improve the respective learned algorithm.

8. The healthcare management system of claim 1, wherein in each clinical analysis module the feature extractor submodule selects relevant healthcare data to predict an adverse medical event for the patient.

9. The healthcare management system of claim 1, wherein the healthcare clinical system comprises a patient database, a message queue subsystem, a notifications and messages service subsystem, SMS service subsystem, or an email service subsystem.

10. The healthcare management system of claim 1, further comprising a patient database is a multi-node server cluster to prevent loss of a software stack or compromise patient safety.

11. The healthcare management system of claim 1,
wherein the wearable sensor comprises three different patient sensors selected from the group of an electrocardiogram (ECG) sensor, a ballistocardiogram (BCG) sensor, a photoplethysmography (PPG) sensor, a skin temperature (TEMP) sensor, a motion and position sensor, electrodermal (EDA) sensor;
wherein the motion and position sensor comprises an accelerometer and a gyroscope;
wherein the three different sensors are operatively integrated on a printed circuit board.

12. The healthcare management system of claim 1, further comprising
a chest band for securing the wearable sensor to a chest of the patient,
a charging pad for wirelessly charging the wearable sensor; and
a haptic feedback device to alert the patient.

13. The healthcare management system of claim 1, further comprising a haptic feedback device to alert the patient to the relay to attend to an information request from the healthcare team.

14. The healthcare management system of claim 1,
wherein the wearable sensor comprises a patient sensor selected from the group of an electrocardiogram (ECG) sensor, a ballistocardiogram (BCG) sensor, a photoplethysmography (PPG) sensor, a skin temperature (TEMP) sensor, a motion and position sensor, and electrodermal (EDA) sensor;
wherein the patient sensor determines measurement data from a signal obtained by the sensor and calculates extracted quantitative data, the extracted quantitative data being transmitted as healthcare data to the healthcare clinical system.

15. The healthcare management system of claim 1, wherein the wearable sensor comprises a ballistocardiogram (BCG) sensor, the BCG sensor being used to calculate a respiration rate, a respiration volume, a heart rate, and a heart stroke volume, and providing data for blood pressure calculations.

16. The healthcare management system of claim 1, wherein the relay and the wearable sensor are in communication via Bluetooth.

17. The healthcare management system of claim 1, wherein the relay and the healthcare clinical system are in communication via a cellular data network.

18. The healthcare management system of claim 1, wherein the wearable sensor and the healthcare clinical system are in communication via a cellular data network.

19. A healthcare management system for a healthcare team caring for a patient to serve a healthcare need of the patient, the healthcare management system comprising:
a wearable sensor worn by the patient for obtaining healthcare data from the patient;

a healthcare clinical system comprising a healthcare analysis subsystem for analyzing the healthcare data; and a relay device in communication selectively with the wearable sensor and the healthcare clinical system;

wherein the healthcare analysis subsystem comprises an artificial intelligence (AI) engine, the AI engine comprising a plurality of clinical analysis modules, each clinical analysis module directed to a respective predetermined medical area, the respective clinical analysis module analyzing the healthcare data with a respective learned algorithm directed to the respective predetermined medical area;

wherein each clinical analysis module comprises the respective learned algorithm and a feature extractor submodule for selecting a data subset from the healthcare data and for performing data transformations from the data subset, the data subset related to the respective predetermined medical area of the clinical analysis module;

wherein each clinical analysis module of the plurality of clinical analysis modules is functionally independent of the AI engine for analyzing the healthcare data, and wherein each clinical analysis module comprises software interfaces for incoming healthcare data and outgoing processed data to integrate the respective clinical analysis module into the AI engine;

wherein the wearable sensor comprises a patient sensor selected from the group of an electrocardiogram (ECG) sensor, a ballistocardiogram (BCG) sensor, a photoplethysmography (PPG) sensor, a skin temperature (TEMP) sensor, a motion and position sensor, and electrodermal (EDA) sensor;

wherein the wearable sensor and the healthcare clinical system are in communication via a data network.

20. A healthcare management system for a healthcare team caring for a patient to serve a healthcare need of the patient, the healthcare management system comprising:

a wearable sensor worn by the patient for obtaining healthcare data from the patient;

a healthcare clinical system comprising a healthcare analysis subsystem for analyzing the healthcare data; and a relay device in communication selectively with the wearable sensor and the healthcare clinical system;

wherein the healthcare analysis subsystem comprises an artificial intelligence (AI) engine, the AI engine comprising a plurality of clinical analysis modules, each clinical analysis module directed to a respective predetermined medical area, the respective clinical analysis module analyzing the healthcare data with a respective learned algorithm directed to the respective predetermined medical area;

wherein each clinical analysis module comprises the respective learned algorithm and a feature extractor submodule for selecting a data subset from the healthcare data and for performing data transformations from the data subset, the data subset related to the respective predetermined medical area of the clinical analysis module, wherein each clinical analysis module of the plurality of clinical analysis modules is functionally independent of the AI engine for analyzing the healthcare data, and wherein each clinical analysis module comprises software interfaces for incoming healthcare data and outgoing processed data to integrate the respective clinical analysis module into the AI engine;

wherein the healthcare clinical system comprises a patient database, a message queue subsystem, a notifications and messages service subsystem, SMS service subsystem, or an email service subsystem, and an electronic medical record system, the electronic medical record system comprising laboratory results related to the healthcare need of the patient.

* * * * *